US012751635B2

(12) United States Patent
Colosi

(10) Patent No.: US 12,751,635 B2
(45) Date of Patent: Oct. 6, 2026

(54) BLOOD FLOW RESTRICTION SYSTEMS HAVING WIRELESS MONITORING AND CONTROL

(71) Applicant: Smart Tools Plus, LLC, Strongsville, OH (US)

(72) Inventor: Nicholas Colosi, Strongsville, OH (US)

(73) Assignee: Smart Tools Plus, LLC, Strongsville, OH (US)

( * ) Notice: Subject to any disclaimer, the term of this patent is extended or adjusted under 35 U.S.C. 154(b) by 1084 days.

(21) Appl. No.: 17/146,659

(22) Filed: Jan. 12, 2021

(65) Prior Publication Data

US 2021/0228099 A1 Jul. 29, 2021

Related U.S. Application Data

(63) Continuation-in-part of application No. 16/773,102, filed on Jan. 27, 2020, now abandoned.

(Continued)

(51) Int. Cl.
*A61B 5/021* (2006.01)
*A61B 5/00* (2006.01)
*A61B 5/022* (2006.01)

(52) U.S. Cl.
CPC ........ *A61B 5/02141* (2013.01); *A61B 5/0015* (2013.01); *A61B 5/02233* (2013.01);

(Continued)

(58) Field of Classification Search
CPC ...... A61H 2201/123; A61H 2201/1654; A61H 2201/165; A61H 11/00; A61H 11/02;

(Continued)

(56) References Cited

U.S. PATENT DOCUMENTS 2,943,859 A 7/1960 Koski et al.
3,906,937 A 9/1975 Aronson (Continued)

FOREIGN PATENT DOCUMENTS

EP 136279 4/1985
EP 2123218 11/2009

(Continued)

OTHER PUBLICATIONS

Datasheet for Venapro (Year: 2015).*

(Continued)

*Primary Examiner* — Brandy S Lee

(74) *Attorney, Agent, or Firm* — UB Greensfelder LLP; Brian E. Turung

(57) ABSTRACT

A BFRT cuff and motor/pump unit and a method for exercising using said cuff. The method incudes providing a BFRT cuff and a motor/pump unit, placing the BFRT cuff on a user's limb, connecting the BFRT cuff to the motor/pump unit, selecting a pressure value or percent of limb occlusion pressure (LOP), causing the motor/pump unit to supply air to the BFRT cuff until the LOP of said limb is obtained, terminating air flow to the BFRT cuff and then reducing the pressure in the BFRT cuff, and exercising the user's limb while the BFRT cuff is at a selected pressure or a selected percent of LOP.

10 Claims, 23 Drawing Sheets

Related U.S. Application Data

(60) Provisional application No. 62/960,957, filed on Jan. 14, 2020, provisional application No. 62/797,689, filed on Jan. 28, 2019.

(52) U.S. Cl.
CPC ................. *A61B 2560/0214* (2013.01); *A61B 2562/0247* (2013.01)

(58) Field of Classification Search
CPC .... A61H 2201/0103; A61H 2201/0176; A61H 2201/1207; A61H 2201/1409; A61H 2201/5007; A61H 2201/5023; A61H 2201/5043; A61H 2201/5071; A61H 2205/06; A61H 2205/10; A61H 9/0092; A63B 21/0085; A41D 1/002; A41D 13/0015; A41D 13/0051; A61B 17/1355; A61B 2017/00132; A61B 2090/032; A61B 2090/064; A61B 2560/0214; A61B 2562/0247; A61B 5/0015; A61B 5/02141; A61B 5/022; A61B 5/02233; A61B 5/6824
See application file for complete search history.

(56) References Cited

U.S. PATENT DOCUMENTS

| | | | | |
|---|---|---|---|---|
| 4,572,205 | A | 2/1986 | Sjonell | |
| 4,621,383 | A | 11/1986 | Gendala | |
| 4,637,394 | A | 1/1987 | Racz et al. | |
| 4,667,672 | A | 5/1987 | Romanowski | |
| 4,928,701 | A | 5/1990 | Harada et al. | |
| 5,022,387 | A | 6/1991 | Hasty | |
| 5,263,473 | A | 11/1993 | McWhorter | |
| 5,584,853 | A | 12/1996 | McEwen | |
| 5,733,304 | A | 3/1998 | Spence | |
| 6,447,467 | B1 | 9/2002 | Barak | |
| 6,478,757 | B1 | 11/2002 | Barak et al. | |
| 6,846,295 | B1 | 1/2005 | Ben-Nun | |
| 7,063,676 | B2 | 6/2006 | Barak et al. | |
| 7,413,527 | B2 | 8/2008 | Sato | |
| 7,455,630 | B2 | 11/2008 | Sato | |
| 7,780,698 | B2 | 8/2010 | McEwen et al. | |
| 8,021,283 | B2 | 9/2011 | Sato et al. | |
| 8,182,403 | B2 | 5/2012 | Sato | |
| 8,273,114 | B2 | 9/2012 | Wasowski | |
| 8,328,693 | B2 | 12/2012 | Sato | |
| 8,366,740 | B2 | 2/2013 | McEwen et al. | |
| 8,419,666 | B2 | 4/2013 | Liu et al. | |
| 8,425,426 | B2 | 4/2013 | McEwen et al. | |
| 8,506,508 | B2 | 8/2013 | Avitable et al. | |
| 8,597,194 | B2 | 12/2013 | Barak et al. | |
| 8,721,575 | B2 | 5/2014 | Brown | |
| 8,740,828 | B2 | 6/2014 | Brown et al. | |
| 8,784,346 | B2 | 7/2014 | Barak et al. | |
| 8,992,397 | B2 | 3/2015 | Sato | |
| 9,107,793 | B2 | 8/2015 | Avitable et al. | |
| 9,114,052 | B2 | 8/2015 | Avitable et al. | |
| 9,301,701 | B2 | 4/2016 | McEwen et al. | |
| 9,386,928 | B2 | 7/2016 | Quinn et al. | |
| 9,387,146 | B2 | 7/2016 | Avitable et al. | |
| 9,788,738 | B2 | 10/2017 | Barak et al. | |
| 9,877,733 | B1 | 1/2018 | Jafary | |
| 10,245,458 | B2 * | 4/2019 | Sato | A63B 21/4025 |
| 10,646,231 | B2 | 5/2020 | McEwen et al. | |
| 10,646,232 | B2 | 5/2020 | McEwen et al. | |
| 2002/0016610 | A1 * | 2/2002 | Hovanes | A61B 17/1355 606/203 |
| 2003/0032905 | A1 | 2/2003 | Waldridge et al. | |
| 2005/0070828 | A1 | 3/2005 | Hampson et al. | |
| 2005/0182331 | A1 | 8/2005 | Millay et al. | |
| 2005/0187501 | A1 * | 8/2005 | Ravikumar | A61F 13/085 601/152 |
| 2006/0270530 | A1 * | 11/2006 | Sato | A63B 24/0087 482/148 |
| 2007/0005106 | A1 * | 1/2007 | Adducci | A61B 17/135 606/202 |
| 2009/0124912 | A1 | 5/2009 | McEwen et al. | |
| 2010/0324429 | A1 | 12/2010 | Leschinsky | |
| 2011/0034762 | A1 | 2/2011 | Paganon | |
| 2011/0125036 | A1 | 5/2011 | Nakajima et al. | |
| 2011/0160022 | A1 | 6/2011 | Sato | |
| 2011/0201979 | A1 * | 8/2011 | Voss | A61H 31/005 601/41 |
| 2013/0031716 | A1 | 2/2013 | Hall et al. | |
| 2013/0138001 | A1 | 5/2013 | Wu | |
| 2014/0142473 | A1 * | 5/2014 | Lowe | A61H 9/0092 601/84 |
| 2014/0155708 | A1 | 6/2014 | Petersen et al. | |
| 2014/0276294 | A1 * | 9/2014 | Mansur, Jr. | A61H 9/0078 601/152 |
| 2014/0303533 | A1 * | 10/2014 | Zeutzius | A61H 9/0092 601/151 |
| 2015/0150560 | A1 | 6/2015 | Sato | |
| 2015/0224012 | A1 * | 8/2015 | Wright | A61H 9/0078 601/150 |
| 2015/0297933 | A1 | 10/2015 | Fukuta | |
| 2015/0351969 | A1 | 12/2015 | Farrow | |
| 2016/0193491 | A1 | 7/2016 | Sato | |
| 2017/0112504 | A1 * | 4/2017 | McEwen | A63B 69/0059 |
| 2017/0224335 | A1 | 8/2017 | Weaner et al. | |
| 2017/0224357 | A1 | 8/2017 | Whalen et al. | |
| 2017/0325825 | A1 | 11/2017 | Bybordi | |
| 2018/0021210 | A1 * | 1/2018 | Stray-Gundersen | A61H 9/0092 601/152 |
| 2018/0290005 | A1 | 10/2018 | Sato | |
| 2020/0297569 | A1 * | 9/2020 | Angelo | A61H 1/006 |

FOREIGN PATENT DOCUMENTS

| | | | |
|---|---|---|---|
| JP | 2012223508 | 11/2012 | |
| WO | 2016087123 | 6/2016 | |
| WO | 2017139508 | 8/2017 | |
| WO | 2017149690 | 3/2018 | |
| WO | 2018069931 | 4/2018 | |
| WO | 2019068147 | 4/2019 | |
| WO | WO-2019068147 A1 * | 4/2019 | A61B 17/1355 |

OTHER PUBLICATIONS

U.S. Appl. No. 61/469,618, filed Nov. 21, 2000, Sato.

US Search Authority, International Search Report and Written Opinion in corresponding application No. PCT/US2021/013029 (Apr. 14, 2021).

US Search Authority, International Search Report and Written Opinion for related application PCT/US2020/015166 (Mar. 24, 2020).

US Search Authority, International Search Report and Written Opinion in corresponding PCT application No. PCT/US2021/013029 (Apr. 24, 2021).

Japanese Office Action of Corresponding Japanese Application No. 2022-543017 dated Sep. 24, 2024, 18 pages.

* cited by examiner

BLOOD FLOW RESTRICTION SYSTEMS HAVING WIRELESS MONITORING AND CONTROL

The present disclosure claims priority on U.S. Provisional Application No. 62/960,957 filed Jan. 14, 2020, which is incorporated herein by reference.

The present disclosure is also a continuation-in-part of U.S. application Ser. No. 16/773,102 filed Jan. 27, 2020, which in turn claims priority on U.S. Provisional Application No. 62/797,689 filed Jan. 28, 2019, which are incorporated herein by reference.

FIELD OF THE DISCLOSURE

This disclosure relates to blood flow restriction systems, specifically to a blood flow restriction system that can be wirelessly monitored and/or controlled, more specifically to a blood flow restriction system that can be wirelessly monitored and/or controlled to a specific percentage of limb occlusion pressure (LOP), and even more specifically to a blood flow restriction system that can be wirelessly monitored and/or controlled to measure the LOP for a particular limb of a user and then set the inflatable belt system to a specific percentage of LOP as set by the user.

BACKGROUND

Blood Flow Restriction Training (BFRT) is becoming a popular tool to improve muscle strength, size, and functional aerobic capacity in shorter amounts of time with less stress on the body than typical training. Practitioners began using BFRT in the treatment and recovery from musculoskeletal injuries or disabilities. Trainers and coaches have used BFRT as an adjunct for a usual training regimen or as a tool to aid recovery. BFRT is the brief and intermittent occlusion or restriction of arterial and venous blood flow performed by applying a tourniquet to the upper or lower extremity. BFRT has been found to augment skeletal muscle adaptation, along with systemic whole body changes and cardiovascular benefits while at rest, with low intensity endurance exercises or low load resistance training. BFRT has been found to be safe when applied with pressures relative to the cuff width and individual limb circumference which is obtained through measuring limb occlusion pressures via a Doppler.

BFRT is done by wrapping a tourniquet around the top portion of one's upper or lower limbs. The wrapping restricts blood flow from the veins of the working muscles to the heart and limits the amount of blood flow to the limbs from the arteries. The restriction results in physiological changes that mimic changes associated with high intensity exercise. The results are gains in muscle size and strength and increases in cardiovascular function at much lower intensities than are usually required for adaptation.

Various types of BFRT cuffs have been developed as described in U.S. Pat. Nos. 6,149,618; 7,413,527; 7,455,630; 8,021,283; 8,182,403; 8,273,114; 8,328,693; 8,366,740; 8,425,426; 8,992,397; 9,301,701; and 10,245,458; US Publication Nos. US 2009/0124912; 2015/0150560; US 2016/0193491; US 2017/0112504; US 2017/0224357; 2017/0325825; and US 2018/0290005; PCT Publication Nos. WO 2016/087123; WO 2017/149690; and WO 2019/068147; and the Smart CuffrM devices offered by Smart Tools Plus, LLC (https://www.smarttoolsplus.com/), all of which are incorporated herein by reference.

Although these prior art BFRT cuffs can be successfully used for BFRT, these prior art BFRT cuffs typically require manual inflation/deflation, use of manual pressure gauges to monitor the pressure of the cuff, and the inconvenient adjustment of the cuff pressure during training. As such, there remains a need for a BFRT cuff having improved convenience of use during BFRT.

SUMMARY

The BFRT system in accordance with the present disclosure is designed/configured to address the continued needs of individuals using BFRT. The BFRT system of the present disclosure includes and/or is used with one or more of the following features:

- a BFRT system that is simple and inexpensive to manufacture;
- a BFRT system that is comfortable for use by the user;
- a BFRT system that is simple to use by the user;
- a BFRT system that is easy to apply and remove by the user;
- a BFRT system that is compact, lightweight, and easy to use, transport and store;
- a BFRT system that is can be used for a wide range of user body types;
- a BFRT system that is washable;
- a BFRT system that is durable;
- a BFRT system including contours to the body when inflated;
- a BFRT system including one or more air chambers;
- a BFRT system that is at least 11 inches long (e.g., 11-30 inches);
- a BFRT system having a urethane-coated air bladder;
- a BFRT system including a motor/pump unit to inflate/deflate the one or more air chambers in the BFRT system;
- a BFRT system including a motor/pump unit to inflate/deflate the one or more air chambers during use of the BFRT system;
- a BFRT system including a motor/pump unit that is detachable/connectable to the BFRT cuff and can remain connected to the BFRT cuff or be removed from the BFRT cuff prior to, during, and/or after use of the BFRT cuff;
- a BFRT system including a battery-powered motor/pump unit;
- a BFRT system including a battery-powered motor/pump unit wherein the battery is rechargeable;
- a BFRT system including a motor/pump unit having one or more displays regarding a) whether the pump is on/off, b) battery status, c) pressure level for pressure in the one or more air chambers of the BFRT cuff, d) time/date, e) whether pressure in the one of more air chambers of the BFRT cuff is at or below limb occlusion pressure, f) error notification/status, g) security status (e.g., locked, unlocked, etc.), h) ambient temperature, i) timer/clock information, j) alarm status/notification, k) time of use, l) pressure mode, operation mode and/or selected training session, m) whether full occlusion has been obtained, n) whether maximum workout time period has occurred, o) wireless connection status to computer, tablet, smart phone, and/or other type of smart device. p) preset value for % LOP, and/or q) preset % value for % LOP;
- a BFRT system including a motor/pump unit that can be manually controlled on the motor/pump unit itself and/or be controlled wired and/or wirelessly by a computer, tablet, smart phone, and/or other type of smart device;

a BFRT system including a motor/pump unit wherein the air pressure in the one or more air chambers can be manually controlled on the motor/pump unit itself and/or be controlled wire and/or wirelessly by a computer, tablet, smart phone, and/or other type of smart device using a computer program or mobile app;

a BFRT system including a motor/pump unit wherein the air pressure in the one or more air chambers can be automatically adjusted for pressure changes during use of the BFRT cuff;

a BFRT system including a motor/pump unit that can remain on the BFRT cuff during exercise or be removed from the BFRT cuff prior to, during, or after the user exercises;

a BFRT system including a pressure sensor and one or more processors to a) facilitate in controlling/maintaining/regulating the pressure in the one or more air chambers of the BFRT cuff, b) provide pressure information on the housing of the motor/pump unit itself or on some other region of the BFRT cuff, and/or c) provide pressure information wired and/or wirelessly to a computer, tablet, smart phone, and/or other type of smart device and have such information displayed using a computer program or mobile app;

a BFRT system that maintains the pressure in the one or more air chambers of the BFRT cuff during use of the BFRT cuff by a user;

a BFRT system that can be manually or automatically operated;

a BFRT system allowing for manual input of a predetermined limb occlusion pressure and using such information to control/maintain/regulate the pressure in the one or more air chambers of the BFRT cuff;

a BFRT system including wired and/or wirelessly receives information regarding the automatic calculation of a predetermined limb occlusion pressure via a computer program or mobile app running on a computer, tablet, smart phone, and/or other type of smart device and using such information to control/maintain/regulate the pressure in the one or more air chambers of the BFRT cuff;

a BFRT system including a sensor to automatically shut off the pump and/or release pressure in the one or more air chambers of the BFRT cuff after sensing that an occlusion pressure in the one or more air chambers has been maintained for some preset period of time (e.g., up to 30 seconds, up to 1 minute, up to 4 minutes, up to 5 minutes, 0.001 seconds to 8 minutes [and all values and ranges therebetween], etc.);

a BFRT system including a sensor to automatically shut off the pump and/or releases pressure in the one or more air chambers of the BFRT cuff after some preset period of time (e.g., 20 minutes, 5 seconds to 30 minutes [and all values and ranges therebetween], etc.);

a BFRT system including a sensor to automatically shut off the pump and/or releases pressure in the one or more air chambers of the BFRT cuff after some preset period of time of non-use of the BFRT cuff (e.g., 10 minutes, 5 seconds to 30 minutes [and all values and ranges therebetween], etc.);

a BFRT system including a GPS sensor or other type of location sensor;

a BFRT system including one or more movement sensors;

a BFRT system including a gyroscope sensor;

a BFRT system including one or more pressure modes (e.g., blood flow restriction mode, ischemic preconditioning mode, manual mode, auto mode, etc.);

a BFRT system that wired and/or wirelessly receives information used to control operation of the BFRT cuff;

a BFRT system that wired and/or wirelessly receives information used to select the mode of operation of the BFRT system (e.g., ischemic preconditioning mode ("IPC"), manual mode, auto mode, etc.);

a BFRT system including a detachable motor/pump unit;

a BFRT system including a pressure port to facilitate in pressure maintenance in the one or more air chambers of the BFRT cuff once the motor/pump unit is detached from the BFRT cuff;

a BFRT system including one or more pressure sensors to control one or more valves to the one or more air chambers in the BFRT cuff to automatically reduce pressure to a set or predetermined pressure for the one or more air chambers in the BFRT cuff;

a BFRT system including a control system for auto-regulation of pressure in the BFRT cuff during use of the BFRT cuff by a user;

a BFRT system including a control system for auto-regulation of pressure in the BFRT cuff within a certain pressure range of a set pressure or set % LOP during use of the BFRT cuff by a user;

a BFRT system including a control system to partially or fully deflate the pressure in the BFRT cuff after the user completes a rep or exercise routine, and then reinflates the BFRT cuff when the user begins a new rep or exercise;

a BFRT system including a control system to partially or fully deflate the pressure in the BFRT cuff after the BFRT cuff immediately detects or detects after a period of time that the user has stopped using the BFRT cuff, and optionally reinflates that BFRT cuff when the BFRT cuff detects use of the BFRT cuff by the user;

a BFRT system including one or more pressure sensors to control one or more valves to the one or more air chambers in the BFRT cuff to automatically reduce pressure to a set or predetermined pressure for the one or more air chambers in the BFRT cuff;

a computer program or mobile app that can run on a computer, server, cloud, tablet, smart phone, and/or other type of smart device that is used to select a BFRT training session, keep track of BFRT training sessions, provide suggested training tips for BFRT, provide suggested BFRT sessions, etc.; and/or a computer program or mobile app that can run on a computer, server, cloud, tablet, smart phone, and/or other type of smart device that uses password and/or other security controls to prevent unauthorized use of the BFRT system and/or access to personal information regarding the use of the BFRT system.

In another and/or alternative non-limiting aspect of the present disclosure, there is provided a BFRT system including a motor/pump unit that includes a) a housing; b) a motor; c) a pump; d) one or more displays (e.g., LED screen, OLED screen, etc.) to display measured pressure and/or to display other information; e) optional one or more processors; f) wireless electronics to send/receive wireless signals between the motor/pump unit and a computer, server, data hub, cloud, tablet, smart phone and/or other type of smart device; g) one or more pressure gauges and/or sensors used to measure a gas pressure in the air inflatable system; h) optional power source to power one or more components of the motor/pump unit (e.g., motor, pump, pressure sensor/gauge; electronics, display, etc.); i) optional one or more power ports to charge the power source; j) optional connection arrangement to permanently or releasably connect the motor/pump unit to the outer material cover; k) optional one or more fluid connectors to fluidly connect the motor/pump unit to the air inflatable system; l) optional GPS system; m) optional circuit board and other electronics; n) optional software; o) optional one or more data ports (e.g., micro USB port, etc.) to enable wired transfer of data between the motor/pump unit and a computer, server, data hub, cloud, tablet, smart phone and/or other type of smart device; p) optional one or more buttons (e.g., power button, etc.), q) optional one or more selection or scroll buttons to enable manual operation/control of the motor/pump unit and/or to select certain information to be displayed on the motor/pump unit; q) optional one or more switch(es) to enable manual operation/control of the motor/pump unit; r) optional air hose port; s) optional one or more lights and/or other indicators to indicate a mode and/or operation and/or status of the motor/pump unit; t) optional memory; u) optional gyroscope system to measure/determine/detect movement and/or movement direction of the BFRT cuff during use of the BFRT cuff by a user; and/or v) one or more movement/motion sensors to measure/determine/detect movement and/or movement direction of the BFRT cuff during use of the BFRT cuff by a user.

In another and/or alternative non-limiting aspect of the present invention, the motor/pump unit can be sized and have a weight that can be easily handled by a user. Generally, the volume of the housing of the motor/pump unit is no more than 500 cubic inches, typically 0.5-500 cubic inches (and all values and ranges therebetween), and more typically 1-50 cubic inches. Generally, the weight of the motor/pump unit, including the housing and optional air hose, is no more than 10 lbs., typically 0.05-10 lbs. (and all values and ranges therebetween), and more typically 0.2-3 lbs. Generally, the size and shape of the housing is such that it can be held and carried above a ground surface in a single hand of an average adult user without need of any further assistance or support system. In one specific non-limiting embodiment, the motor/pump unit has a volume of less than 30 cubic inches and a weight of less than 1.5 lbs.

In another and/or alternative non-limiting aspect of the present disclosure, there is provided a BFRT cuff including one or more air bladders that can be inflated and deflated and a detachable air pump configured to inflated and deflate the one or more air bladders of the BFRT cuff. The BFRT cuff is generally formed of a flexible material (e.g., nylon material, neoprene, Kevlar™, etc.) to partially or fully house the one or more air bladders. The one or more air bladders can be formed of a rubber material or any other material that can be inflated and retain air within the air bladder until deflated. The length of the BFRT cuff is generally 20-70 cm (and all values and ranges therebetween) for use about an arm and generally 30-100 cm (and all values and ranges therebetween) for use about a leg; however, other lengths can be used. The width of the BFRT cuff is at least 5 cm, typically about 5-14 cm (and all values and ranges therebetween), and more typically about 8-12 cm; however, other widths can be used. The BFRT cuff includes one or more air connection arrangements to inflate/deflate the one or more air bladders. Generally, the one or more air connection arrangements are configured to releasably connect to a pump or air tube to inflate/deflate the one or more air bladders. In one non-limiting arrangement, the one or more air connection arrangements are a quick-connect arrangement known in the art. The BFRT cuff generally includes one or more valves to maintain and/or release air from the one or more air bladders. In one non-limiting arrangement, the air connection arrangements include one or more valves.

In another and/or alternative non-limiting aspect of the present disclosure, there is provided a motor/pump unit to inflate and/or deflate the one or more air bladders in the BFRT cuff. In one non-limiting embodiment, the housing of the motor/pump unit includes a rechargeable battery. The rechargeable battery can be charged wirelessly and/or via a charge cable. The housing optionally includes a charging port for the rechargeable battery. The motor/pump unit can include an air tube connected at one end to the housing of the motor/pump unit and configured to be connected (e.g., releasably connected, non-releasably connected, etc.) at the other end to an air connection arrangement on the BFRT cuff.

In another and/or alternative non-limiting aspect of the present disclosure, the motor/pump unit includes a sensor to detect the air pressure in the one or more air bladders of the BFRT cuff. The motor/pump unit typically includes electronics (e.g., processor, software code, logic circuits, etc.) that facilitate in the measurement calculations for pressure.

In another and/or alternative non-limiting aspect of the present disclosure, the housing of the motor/pump unit includes a display and one or more user interface buttons. The one or more buttons can include a) a power button, b) one or more arrow or scroll up/down buttons, and/or c) a reset button. The display can be a LED display or the like, and may or may not be a touch screen display. Information on the display can include, but is not limited to, a) battery power level, b) pressure reading, c) warning indicator for too high pressure, d) warning indicator for too low pressure, e) waring indicator of pressure above or below preset % LOP, f) warning indicator for battery level too low, g) information about BFRT, h) arm or leg selection, i) limb occlusion pressure (LOP), j) day and/or time, k) time BFRT cuff pressurized, 1) pressure reset, m) system reset, n) deflate BFRT cuff, o) inflate BFRT cuff, p) percent of LOP to which BFRT cuff is to be pressurized, q) preset range of operation for preset % LOP, etc.

In another and/or alternative non-limiting aspect of the present disclosure, the motor/pump unit is configured to 1) pressurize the BFRT cuff until a LOP pressure is reached or a maximum preset pressure (e.g., 400 mmHg, 100-500 mmHg [and all values and ranges therebetween], etc.) is reached, 2) reduce the pressure in the BFRT cuff to a set percent of LOP (% LOP) (e.g., preset % LOP or manually set % LOP), and 3) terminate operation of the air pump after the set % LOP is obtained or after a maximum preset pressure has been obtained.

In another and/or alternative non-limiting aspect of the present disclosure, the BFRT system is configured to maintain the pressure (e.g., Auto Regulate pressure) in the one or more air chambers of the BFRT cuff at a preselected pressure or within a set % LOP during use of the BFRT cuff by a user. During use of the BFRT system, the BFRT system can maintain the pressure in one or more air chambers in the BFRT cuff at a preselected value or a preselected pressure range. For example, a user can preset the pressure in the one or more air chambers in the BFRT cuff at a certain % LOP, at a certain range of % LOP, a certain pressure, and/or at a certain range of pressure. In one non-limiting arrangement, a user can preset or the BFRT system can automatically create a preset for a certain % LOP at which the one or more air chambers in the BFRT cuff are to be inflated during the use of the BFRT cuff by a user, and if one or more pressure sensors detect the pressure in the one or more air chambers exceeding the preset % LOP, the BFRT system causes gas (e.g., air, etc.) to be released from the one or more air chambers until the one or more pressure sensors detect a pressure in the one or more air chambers that indicates that the pressure is now at the preset % LOP, and if one or more pressure sensors detect the pressure in the one or more air chambers below the preset % LOP, the BFRT system causes gas (e.g., air, etc.) to be inserted into the one or more air chambers until the one or more pressure sensors detect a pressure in the one or more air chambers that indicates that the pressure is now at the preset % LOP. In one non-limiting arrangement, a user can preset or the BFRT system can automatically preset create a preset for a certain range of % LOP (e.g., 5-99% of LOP [and all values and ranges therebetween]) or to be within a certain range (±0.001% to ±10% [and all values and ranges therebetween]) of a pre-selected % LOP that the one or more air chambers in the BFRT cuff are to be inflated during the use of the BFRT cuff by a user, and if one or more pressure sensors detect the pressure in the one or more air chambers exceeding the preset range of LOP % or exceeding the preset range of the preset LOP %, the BFRT system causes gas (e.g., air, etc.) to be released from the one or more air chambers until the one or more pressure sensors detect a pressure in the one or more air chambers that indicates that the pressure is now within the present range of LOP % or within the preset range of the present LOP %, and if one or more pressure sensors detect the pressure in the one or more air chambers below the preset range of LOP % or below the preset range of the preset LOP %, the BFRT system causes gas (e.g., air, etc.) to be inserted into the one or more air chambers until the one or more pressure sensors detect a pressure in the one or more air chambers that indicates that the pressure is now within the present range of LOP % or within the preset range of the present LOP %.

In another and/or alternative non-limiting aspect of the present disclosure, the BFRT system is configured to maintain the pressure (e.g., Auto Regulate pressure) in the one or more air chambers of the BFRT cuff within a range of a preselected pressure or within a set % LOP during use of the BFRT cuff by a user. For example, a user can preset the pressure in the one or more air chambers in the BFRT cuff at a certain % LOP when the BFRT cuff is attached to an arm of the user (e.g., arm—30% LOP-50% LOP and all values and ranges therebetween) and the BFRT system then maintains the pressure in the one or more air chambers of the BFRT cuff within a certain range encompassing the preset % LOP (e.g., 20% LOP—60% LOP and all values and ranges therebetween). In one specific example, the BFRT cuff is attached to the user's arm. The BFRT system is set by the user to use a 35% LOP for the BFRT cuff during use of the BFRT cuff by the user. The BFRT cuff then inflates the BFRT cuff to determine the LOP pressure, and then releases the pressure in the BFRT cuff until the pressure in the BFRT cuff is 35% LOP. While the user exercises his/her arm that includes the BFRT cuff, the pressure in the BFRT cuff increases and decreases during arm extension exercise. When the arm is bent, the muscles in the arm cause compression on the BFRT cuff, thereby causing an increase in pressure in the BFRT cuff. If the detected pressure exceeds an upper % LOP setting (e.g., 60% LOP), the BFRT system causes the pressure in the BFRT cuff to decrease so as to fall below the upper % LOP setting. When the arm is extended, the muscles in the arm decrease compression on BFRT cuff, thereby causing a decrease in pressure in the BFRT cuff. If the detected pressure is below a lower % LOP setting (e.g., 20% LOP), the BFRT system causes the pressure in the BFRT cuff to increase to cause the pressure to be above the lower % LOP setting. As can be appreciated, the selected % LOP for a particular arm exercise can be manually set by a user or be automatically set by the BFRT system. Also, the upper % LOP and/or lower % LOP for a particular arm exercise can be manually set by a user or be automatically set by the BFRT system. In another example, a user can preset the pressure in the one or more air chambers in the BFRT cuff at a certain % LOP when the BFRT cuff is attached to a leg of the user (e.g., leg—50% LOP-80% LOP and all values and ranges therebetween) and the BFRT system maintains the pressure in the one or more air chambers of the BFRT cuff within a certain range encompassing the preset % LOP (e.g., 40% LOP—90% LOP and all values and ranges therebetween). In one specific example, the BFRT cuff is attached to the user's leg. The BFRT system is set by the user to use a 60% LOP for the BFRT cuff during use of the BFRT cuff. The BFRT cuff then inflates the BFRT cuff to determine the LOP pressure, and then releases the pressure in the BFRT cuff until the pressure in the BFRT cuff is 60% LOP. While the user exercises his/her leg that includes the BFRT cuff, the pressure in the BFRT cuff increases and decreases during a leg extension exercise. When the leg is bent, the muscles in the leg cause compression on the BFRT cuff, thereby causing an increase in pressure in the BFRT cuff. If the detected pressure exceeds an upper % LOP setting (e.g., 90% LOP), the BFRT system causes the pressure in the BFRT cuff to decrease to fall below the upper % LOP setting. When the leg is extended, the muscles in the leg decrease compression on BFRT cuff, thereby causing a decrease in pressure in the BFRT cuff. If the detected pressure is below a lower % LOP setting (e.g., 40% LOP), the BFRT system will cause the pressure in the BFRT cuff to increase so as to cause the pressure to be above the lower % LOP setting. As can be appreciated, the selected % LOP for a particular leg exercise can be manually set by a user or be automatically set by the BFRT system. Also, the upper % LOP and/or lower % LOP for a particular leg exercise can be manually set by a user or be automatically set by the BFRT system.

In another and/or alternative non-limiting aspect of the present disclosure, the BFRT system is configured have Intermittent Regulation to partially or fully deflate the one or more air chambers of the BFRT cuff when the BFRT system detects that 1) the user is not using the BFRT cuff, or 2) a set exercise is completed and/or a set number of repetitions (reps) is completed. This Intermittent Regulation feature ensures that the BFRT cuff is partially or fully deflated between exercise sets or reps, or when the BFRT cuff is not being used. In one specific example, the BFRT cuff is attached to the user's arm. The user manually selects an exercise routine or enters a custom exercise routine. The BFRT cuff is inflated to determine the LOP pressure, and then releases the pressure in the BFRT cuff until the pressure in the BFRT cuff is reduced to some % LOP. While the user exercises his/her arm that includes the BFRT cuff, the pressure in the BFRT cuff increases and decreases during an arm extension exercise. Such increase and decrease in pressure is used by the BFRT system to 1) determine whether the BFRT cuff is being used, and/or 2) determine a number of user's reps during an exercise routine. If the BFRT system determines that the BFRT cuff is not being used after a certain period of time (e.g., 2-120 seconds and all values and ranges therebetween, 4-10 seconds, etc.), the BFRT system can be design to partially or fully deflate the BFRT cuff until use is again detected and/or a new exercise routine is started by the user or automatically started by the BFRT system. In one non-limiting example, the BFRT system is designed to deflate the BFRT cuff to 0% LOP to 19.9% LOP (and all values and ranges therebetween) when the BFRT cuff is attached to the arm and the BFRT system determines that the BFRT cuff is not being used after a certain period of time. In another non-limiting example, the BFRT system is designed to deflate the BFRT cuff to 0% LOP to 39.9% LOP (and all values and ranges therebetween) when the BFRT cuff is attached to the leg and the BFRT system determines that the BFRT cuff is not being used after a certain period of time. As can be appreciated, the deflation % LOP when the BFRT system determines that the BFRT cuff is not being used after a certain period of time can be manually set by a user or be automatically set by the BFRT system. Also, the time period that the BFRT system uses to determine non-use b can be manually set by a user or be automatically set by the BFRT system. In another non-limiting example, when the BFRT system is designed to partially or fully deflate the BFRT cuff after the BFRT system has determined that 1) the number of reps selected by the user has been completed, and/or 2) a selected exercise routine has been completed by the user, the time period before the BFRT system allows the user to again have the BFRT cuff inflated for another exercise routine can be a manually selected time period or a preprogramed time period. Generally, such time period is 5 seconds to 4 minutes (and all values and ranges therebetween), and typically 30 seconds to 3 minutes, and more typically 1-2 minutes.

In another and/or alternative non-limiting aspect of the present disclosure, the BFRT system can include preprogrammed exercise routines for the arm and/or leg.

In another and/or alternative non-limiting aspect of the present disclosure, the BFRT system can allow the user to customize and/or manually input exercise routines for the arm and/or leg.

In another and/or alternative non-limiting aspect of the present disclosure, the BFRT cuff can have a urethane-coated air bladder. The urethane coating on the bladder adds to user comfort by reducing pinching of the skin by the bladder when inflated. The urethane coating can also optionally fill in the folds created by the bladder when inflated.

In another and/or alternative non-limiting aspect of the present disclosure, one non-limiting method of operation of the motor/pump unit and BFRT cuff is as follows: a) removably placing a BFRT cuff (e.g., using a hook and loop strap fastener, etc.) onto a user's limb (e.g., arm, leg, etc.), b) attach the pump or pump air hose/tube to the BFRT cuff if not already connected, c) turning on motor/pump unit if not already on, d) optionally allow or cause the motor/pump unit to calibrate to ambient pressure, e) optionally select limb (arm, leg, etc.) on the motor/pump unit (e.g., select limb listed on display of housing of the motor/pump unit, etc.), f) select % LOP (e.g., using display and one or more selection keys on housing of the motor/pump unit, the user selects a desired % LOP or a default % LOP can be selected by the user), which % LOP is generally 20%-80% and all values therebetween of the LOP, g) cause air pump to be activated to pressurize BFRT cuff until the LOP on the limb is detected, h) cause air pump and/or motor/pump unit to reduce pressure in the BFRT cuff until the selected % LOP is detected in the BFRT cuff, i) terminate operation of the air pump after the % LOP in the BFRT cuff is obtained, and j) optionally disconnect the air pump or the air hose/tube from the BFRT cuff. The % LOP is obtained in the BFRT cuff by the motor/pump unit first pressurizing the BFRT cuff until the LOP of the limb is detected and thereafter removing or allowing air to be removed from the BFRT cuff until the % LOP is obtained. The air pump typically immediately stops inflating the BFRT cuff once LOP in the limb is detected and thereafter causes the deflation of the BFRT cuff to the selected % LOP. For example, if LOP is detected at a pressure of 200 mmHg, then 50% LOP would be 100 mmHg and 75% LOP would be 150 mmHg. After the user completes use of the BFRT cuff when inflated to the selected % LOP, the user can a) manually partially or fully deflate the BFRT cuff and thereafter remove the BFRT cuff from the limb, or b) have the motor/pump unit partially or fully deflate the BFRT cuff and thereafter remove the BFRT cuff from the limb. If the motor/pump unit is not connected to the BFRT cuff, the motor/pump unit is first connected to the BFRT cuff prior to having the motor/pump unit partially or fully deflate the BFRT cuff.

One non-limiting object of the present disclosure is the provision of a method for exercising using a blood flow restriction training (BFRT) cuff comprising: (a) providing a BFRT cuff, said BFRT cuff formed of a flexible outer material, an air chamber at least partially encapsulated by said flexible outer material, an air input port in fluid communication with said air chamber, and a connection strap configured to secure said BFRT cuff to a limb of a user, at least a portion of said air input port positioned on an exterior surface of said BFRT cuff, said air input port including an air valve, said flexible outer material having a length of at least 20 cm and a width of least 5 cm; (b) providing a motor/pump unit, the motor/pump unit configured to at least partially inflate said BFRT cuff, the motor/pump unit including a housing and an air connection arrangement that fluidly connects said housing to said BFRT cuff via said air input port to enable pumped air from the motor/pump unit to flow to and at least partially inflate said BFRT cuff, said housing having a size less than 400 cubic inches and a weight less than 40 ounces, said housing at least partially contains i) pump (e.g., an electric air pump, etc.), ii) a power source, and iii) a pressure sensor; (c) placing said BFRT cuff on a user's limb; (d) connecting said BFRT cuff to the motor/pump unit to enable air flow between said BFRT cuff the motor/pump unit; (e) selecting a pressure value or percent of LOP, said pressure value less than said LOP, said percent no more than 90%; (f) causing the motor/pump unit to supply air to said BFRT cuff thereby causing said BFRT cuff to inflate until said LOP of said limb is obtained; (g) terminating air flow from the motor/pump unit to said BFRT cuff after said LOP has been obtained for the limb; (h) causing the motor/pump unit to begin reducing pressure in said BFRT cuff within 10 seconds after said LOP is obtained in said BFRT cuff and continue reducing pressure in said BFRT cuff until said pressure value that was selected or said percent of said LOP that was selected is obtained in said BFRT cuff; (i) optionally disconnecting said BFRT cuff from the motor/pump unit so that the motor/pump unit cannot supply air to said BFRT cuff; and, (j) exercising the user's limb while said BFRT cuff is at the selected pressure or the selected percent of said LOP.

Another and/or alternative non-limiting object of the present disclosure is the provision of a method for exercising using a BFRT cuff that further includes the steps of: (k) reconnecting said BFRT cuff to the motor/pump unit to enable air flow between said BFRT cuff the motor/pump unit after the user has completed use of said BFRT cuff on the limb at said pressure value that was selected or said percent of said LOP that was selected; and, (l) causing the motor/pump unit to remove air from said BFRT cuff to reduce pressure in said BFRT cuff below said pressure value that was selected or said percent of said LOP that was selected.

Another and/or alternative non-limiting object of the present disclosure is the provision of a method for exercising using a blood flow restriction training (BFRT) cuff that further includes the step of removing said BFRT cuff from said limb after said step of exercising the user's limb.

Another and/or alternative non-limiting object of the present disclosure is the provision of a method for exercising using a blood flow restriction training (BFRT) cuff wherein said housing of the motor/pump unit includes a circuit board, a processor, a display, a power button, and one or more selection or scroll buttons, said one or more selection or scroll buttons configured to enable manual operation and/or control of the motor/pump unit, said display displaying three or more types of information selected from the group consisting of a) measured pressure, b) power or charge level of said power source, c) a warning symbol when some type of warning event has occurred, d) selected % LOP, e) selected pressure, f) instructional information as to how to use the motor/pump unit and/or BFRT cuff, and g) arm or leg selection options for BFRT cuff.

Another and/or alternative non-limiting object of the present disclosure is the provision of a method for exercising using a BFRT cuff further including the step of turning on or powering up the motor/pump unit, the motor/pump unit configured to calibrate with ambient pressure after the motor/pump unit is turned on or powered up.

Another and/or alternative non-limiting object of the present disclosure is the provision of a method for exercising using a BFRT cuff that further includes the step of selecting the limb upon which said BFRT cuff is to be place.

Another and/or alternative non-limiting object of the present disclosure is the provision of a method for exercising using a BFRT cuff that includes the steps of a) providing a BFRT cuff, said BFRT cuff including i) a flexible outer material, ii) an air chamber at least partially encapsulated by said flexible outer material, and iii) a connection arrangement configured to secure said BFRT cuff to a limb of a user, said flexible outer material having a length of at least 20 cm and a width of least 5 cm; b) providing a motor/pump unit, the motor/pump unit configured to at least partially inflate said BFRT cuff, the motor/pump unit including a housing and an air connection arrangement that fluidly connects said housing to said BFRT cuff to enable pumped air from the motor/pump unit to flow to and at least partially inflate said BFRT cuff, said housing having a size less than 400 cubic inches and a weight less than 4 lbs., said housing at least partially containing i) an air pump, ii) a power source, and iii) a pressure sensor; c) placing said BFRT cuff on a user's limb; d) connecting said BFRT cuff to the motor/pump unit to enable air flow between said BFRT cuff and the motor/pump unit; e) selecting a pressure value or percent of limb occlusion pressure (LOP), said pressure value less than said LOP, said percent no more than 90%; f) causing the motor/pump unit to supply air to said BFRT cuff to thereby cause said BFRT cuff to inflate until said LOP of said limb is obtained; g) terminating air flow from the motor/pump unit to said BFRT cuff after said LOP has been obtained for the limb; h) reducing pressure in said BFRT cuff within 0.001-30 seconds after said LOP is obtained in said BFRT cuff until said pressure value is said selected pressure value or said percent of said LOP; and, i) exercising the user's limb while said BFRT cuff is at said selected pressure value or said selected percent of said LOP; and wherein the motor/pump unit automatically activates said air pump when said pressure in said air chamber falls a certain amount below said selected pressure value or said percent of said LOP during said step of exercising to increase said pressure in said air chamber to said selected pressure value or said percent of said LOP.

Another and/or alternative non-limiting object of the present disclosure is the provision of a method for exercising using a BFRT cuff that includes the steps of a) providing a BFRT cuff, said BFRT cuff formed of a flexible outer material, an air chamber at least partially encapsulated by said flexible outer material, an air input port in fluid communication with said air chamber, and a connection strap configured to secure said BFRT cuff to a user's limb, at least a portion of said air input port positioned on an exterior surface of said BFRT cuff, said air input port including an air valve, said flexible outer material having a length of at least 20 cm and a width of least 5 cm; b) providing a motor/pump unit, said motor/pump unit configured to at least partially inflate said BFRT cuff, the motor/pump unit including a housing and an air connection arrangement that fluidly connects said housing to said BFRT cuff via said air input port to enable pumped air from the motor/pump unit to flow to and at least partially inflate said BFRT cuff, said housing having a size less than 400 cubic inches and a weight less than 4 lbs., said housing at least partially containing i) an electric air pump, ii) a power source, and iii) a pressure sensor; c) placing said BFRT cuff on a user's limb; d) connecting said BFRT cuff to the motor/pump unit to enable air flow between said BFRT cuff and the motor/pump unit; e) selecting a pressure value or percent of limb occlusion pressure (LOP), said pressure value less than said LOP, said percent no more than 95% of LOP (e.g., 5-95% and all values and ranges therebetween], 50-90%, etc.); f) causing the motor/pump unit to supply air to said BFRT cuff to thereby cause said BFRT cuff to inflate until said LOP of said limb is obtained; g) terminating air flow from the motor/pump unit to said BFRT cuff after said LOP has been obtained for the limb; h) causing the motor/pump unit to begin reducing pressure in said BFRT cuff within some preset time (e.g., 0.001-2 minutes [and al values and ranges therebetween], 0.001-10 seconds, etc.] after said LOP is obtained in said BFRT cuff and continue to reduce pressure in said BFRT cuff until said pressure value that was selected or said percent of said LOP that was selected is obtained in said BFRT cuff; i) optionally disconnecting said BFRT cuff from the motor/pump unit so that the motor/pump unit cannot supply air to said BFRT cuff; j) optionally maintaining the motor/pump unit on the BFRT cuff, and optionally enabling the motor/pump unit to maintain/control a pressure of the BFRT cuff (e.g., Auto Regulation of pressure) during use; k) exercising the user's limb while said BFRT cuff is at the selected pressure or the selected percent of said LOP, and 1) optionally providing Intermittent Regulation of pressure of the BFRT cuff.

Other objects, advantages, and novel features of the present disclosure will become apparent from the following description of the disclosure when considered in conjunction with the accompanying drawings.

DETAILED DESCRIPTION

Figure 1:
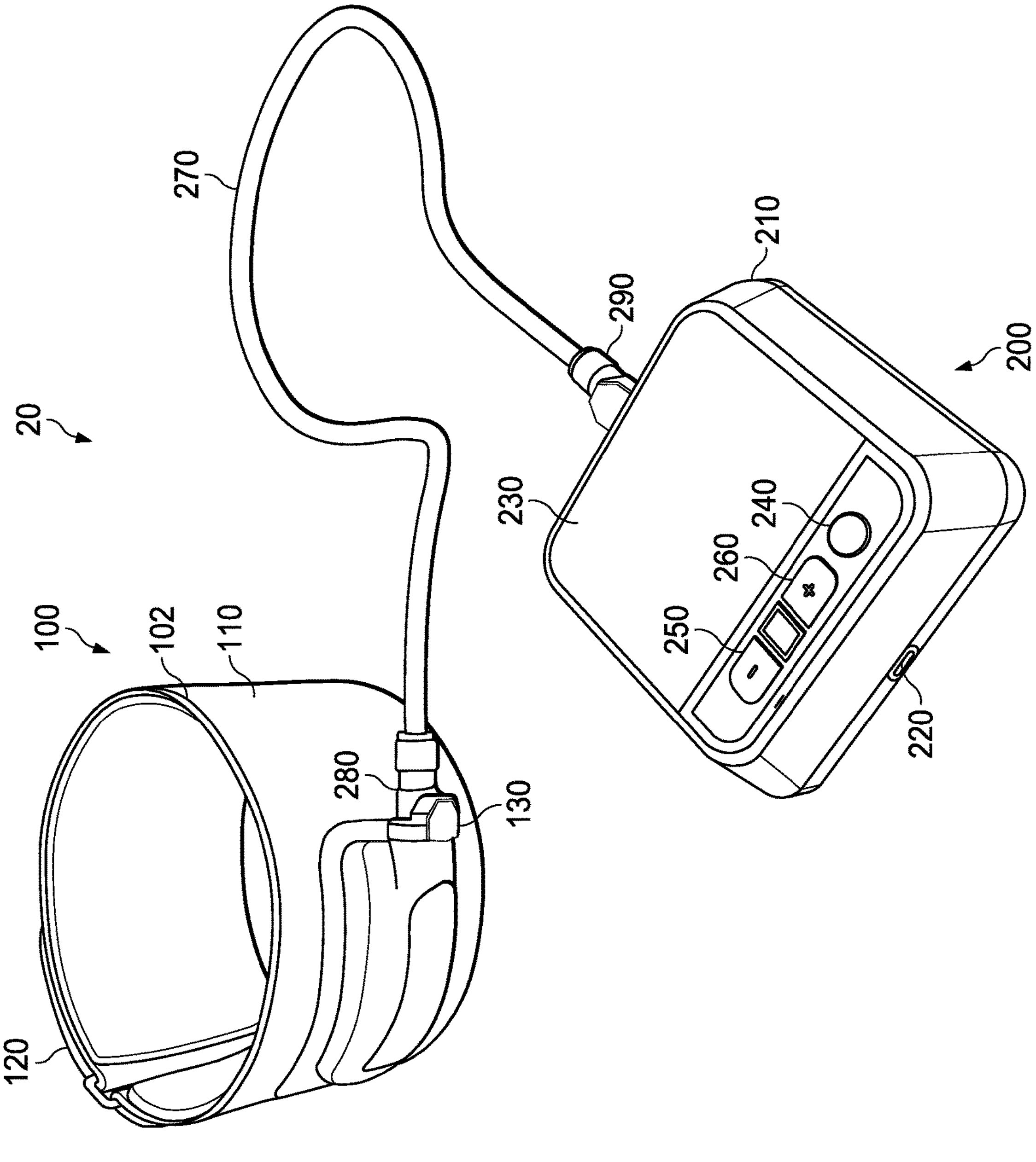
FIGS. 1 and 1A illustrate two BFRT cuffs and a motor/pump unit for each of the BFRT cuffs in accordance with the present disclosure.
Figure 1A:
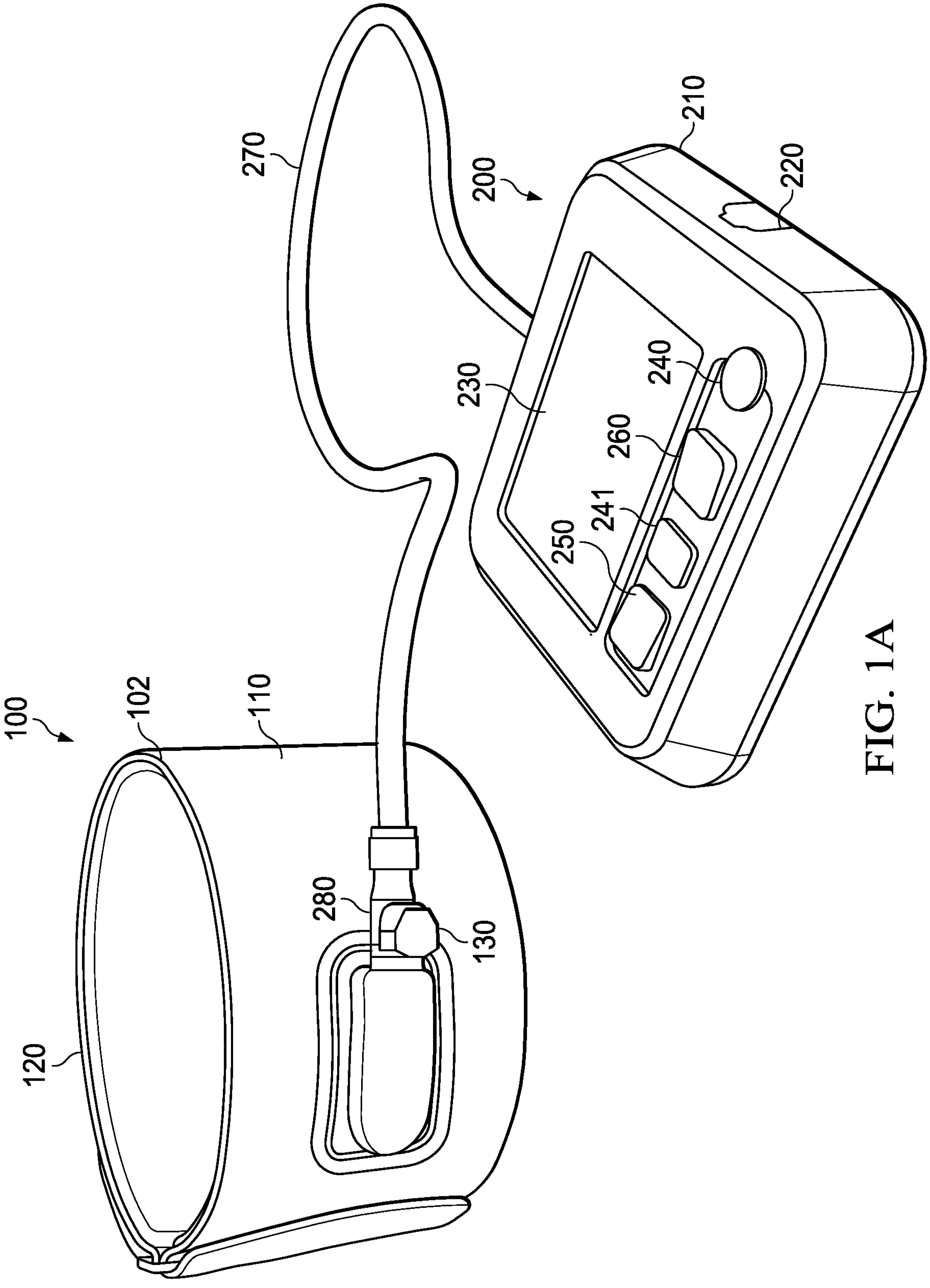

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 inches to 10 inches" is inclusive of the endpoints, 2 inches and 10 inches, and all the intermediate values).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

In accordance with the present disclosure, there is provided a BFRT system 20 that includes a BFRT cuff 100 and motor/pump unit 200.

BFRT 100 cuff includes an inflatable air system formed of one or more two layers of material. In one non-limiting embodiment, the inflatable air system includes two layers of material coupled together to create one or more air chambers to be inflated with air and/or some other gas. In one non-limiting configuration, BFRT cuff 100 is a single air chamber inflatable cuff. In another non-limiting configuration, BFRT cuff 100 includes two or more air chambers. The configuration and shape of the one or more air chambers is non-limiting. The inflatable air system is configured in BFRT cuff 100 such that inflation of the inflatable air system produces compression on a target compression zone that in turn produces a restriction of blood flow in the venous system of a user. BFRT cuff 100 includes an outer material cover 102 having a cavity (not shown) for containing the inflatable air system to partially or fully isolate the inflatable air system from the skin of the user and/or to provide protection to the inflatable air system, and/or to provide structural strength to BFRT cuff 100. The inflatable air system can optionally be secured in the cavity to one or more inner surface of outer material cover 102 (e.g., stitching, adhesive, melted connection, etc.). Oter material cover 102 is generally made of a flexible and durable material (e.g., nylon, Kevlar™, etc.). In one non-limiting embodiment, outer material cover 102 is formed of an inelastic or non-stretch material. Outer material cover 102 is configured to a) facilitate in distributing the force applied by the inflatable air system to the limb of a user, b) reduce pinching of the user's skin during the inflation of the inflatable air system, and/or c) provide friction between BFRT cuff 100 and the user's skin to inhibit or prevent rotation of BFRT cuff 100 on the user during use.

BFRT cuff 100 generally includes a connection arrangement to facilitate in the securing of BFRT cuff 100 to a user's limb. As illustrated in 1, BFRT cuff 100 includes a loop/loop like material 110 on the outer surface that is configured to releasably connect to a book/loop material on a strap 120.

BFRT cuff 100 includes one or more input ports 130 (e.g., air input port, data/communication input port, power input port, etc.). The one or more input ports can be in fluid communication with the inflatable air system to allow a fluid (e.g., air) to flow into and out of the inflatable air system. Input port 130 generally includes a valve component (not shown). The location of the one or more input ports 130 on the BFRT is non-limiting. Generally, at least one input port 130 is located on an outwardly facing surface of the outer material cover 102. One or more of the input ports 130 is configured to be connected to a motor/pump unit 200 (e.g., portable motor/pump, non-portable motor/pump, permanently connected motor/pump, detachably connected motor/pump, etc.). The one or more input ports 130 can optionally include a one-way valve (not shown) to prevent undesired deflation of the air inflatable system. The one or more input ports 130 can optionally be configured to allow for manual deflation of the air inflatable system.

As illustrated in FIGS. 1, 1A, 2 and 3, the BFRT cuff 100 has a motor/pump unit 200 connected to an outer surface 112 of outer material cover 110. In particular, the outer material cover 110 includes a first end 114 and second end 116 and the motor/pump unit 200 is connected to a portion of the outer material cover located closest to first end 114. As can be appreciated, the motor/pump unit 120 can be located on any portion of the outer material cover 110. Although not shown, the outer material cover 110 is connected to an input port so the motor/pump unit 120 can inflate/deflate the BFRT cuff 100.

Motor/pump unit 200 includes a housing 210 that at least partially contains a) a motor (not shown); b) a pump (not shown); c) optionally a power source (not shown); d) one or more pressure sensors (not shown); e) circuit board and other electronics (not shown); f) one or more processors (e.g., controller, etc.); g) one or more pressure gauge(s) (not shown); h) software (not shown); i) one or more display(s) 230 (e.g., LED screen, OLED screen, etc.); j) optionally a power port (not shown); k) optionally a data port 220 (e.g., micro USB port, etc.); l) optional GPS system (not shown); m) optional wireless electronics (e.g., transmitter and/or receiver, etc.) to send/receive wireless signals (not shown); n) one or more buttons 240, 241 (e.g., power button, home button, power off button, etc.); o) one or more selection or scroll buttons 250, 260 to enable manual operation/control of motor/pump unit 200; p) one or more switch(es)(not shown) to enable manual operation/control of motor/pump unit 220; q) connection arrangement 280 to permanently or releasably connect motor/pump unit 220 to the outer material cover 110; r) air hose port 290; and/or s) optional lights and/or other indicators (not shown) to indicate a mode and/or operation and/or status of motor/pump unit 200. The shape and size of housing 210 is non-limiting. The material used to form housing 210 is generally a durable material (e.g., plastic, metal, composite, etc.). Motor/pump unit 200 is generally a portable motor/pump unit 200 that can be easily handled by a user. Generally, the volume of housing 210 of motor/pump unit 200 is no more than 500 cubic inches, typically 0.5-500 cubic inches (and all values and ranges therebetween), and more typically 1-50 cubic inches. Generally, the weight of motor/pump unit 200, including housing 210 and air hose 270, is no more than 10 lbs., typically 0.05-10 lbs. (and all values and ranges therebetween), and more typically 0.2-3 lbs.

As illustrated in FIG. 1, a first end of an air hose 270 is connected to the air hose port 290 on housing 210. Air hose 270 can be permanently or detachably connected to the housing 210. The second end of air hose 280 includes a hose connector 280 configured to releasably connect to air input port 130 on BFRT cuff 100. Generally, the type of connection between hose connector 280 and air input port 130 is a quick-connect connection arrangement; however, this is not required.

Figure 3:
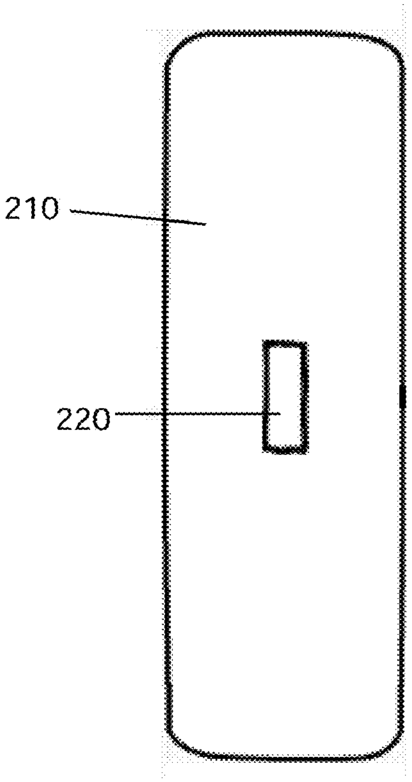
FIG. 3 is a front view of a non-limiting housing of the motor/pump unit of FIG. 1.

As illustrated in FIGS. 1 and 3, the front face of housing 210 includes a power port/data port 220. The type of connection is non-limiting. As can be appreciated, the power port/data port 220 can be located on other regions of housing 220. The power port/data port 220 can optionally recharge the optional battery in the housing 210 and/or power the motor/pump unit 200. The power port/data port 220 can optionally 1) provide software updates to the motor/pump unit 200 and/or allow for repair/reset of the motor/pump unit 200, 2) obtain use/diagnostic information from the motor/pump unit 200, and/or 3) download/upload user information and/or BFRT use information.

Figure 2:
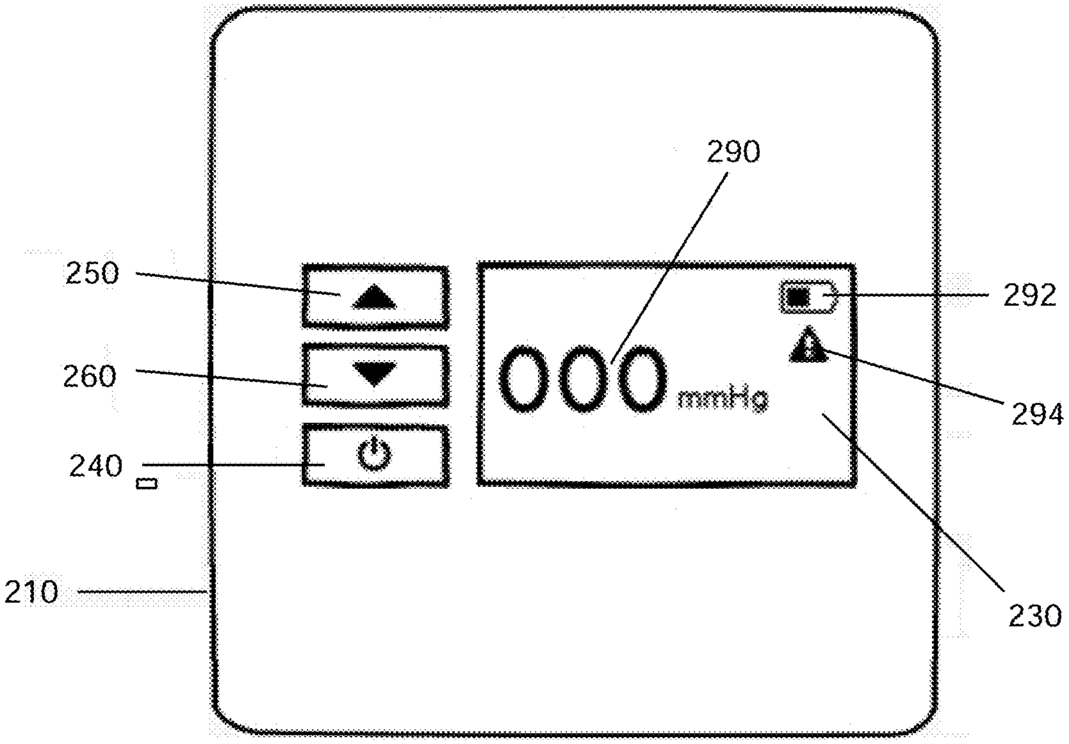
FIG. 2 illustrates a top view of a non-limiting display on the housing of the motor/pump unit of FIG. 1.

As illustrated in FIGS. 1 and 2, two types of button and display configurations are illustrated. As can be appreciated, other types of button and display configurations can be used on housing 210 of motor/pump unit 200. As illustrated in FIG. 1, the top of housing 210 includes a large display 230 covering about 50-80% (and all values and ranges therebetween) of the top surface of the housing 210. The display 230 can be a LED display or the like. Positioned below the display 230 is a power button 220 and two arrow or scroll buttons 250, 260. The power button turns the motor/pump unit 200 on and off. The power button 220 can also optionally reset the motor/pump unit 200. The two arrow or scroll buttons 250, 260 can be used to select items displayed on the display 230 (e.g., select % LOP, select if BFRT cuff is to be used on leg or arm, select time of exercise, select if % LOP used on one limb is to be also used on another limb, deflate BFRT cuff, inflate BFRT cuff, reset motor/pump unit 200, select day, select time, remove/reset warning on display, perform diagnostics on motor/pump unit 200, update on motor/pump unit 200 software/firmware, cause BFRT cuff to be pressurized to LOP for a user limb and then to depressurize BFRT cuff to selected or programmed % LOP, activate/deactivate wireless mode, wirelessly pair motor/pump unit 200 with BFRT cuff 100, select mode of operation of motor/pump unit 200, unlock/lock motor/pump unit 200 to BFRT cuff 100, set inflation pressure, set automatic pressure maintaining mode, etc.). As can be appreciated, the arrow or scroll buttons 250, 260 can be used for other or additional functions.

As illustrated in FIG. 3, the top of the housing 210 includes a display 230, a power button 240, and two arrow or scroll buttons 250, 260; however, the orientation of the display 230 and two arrow or scroll buttons 250, 260 on the top of the housing is different. The size of the display in FIG. 3 is smaller than in FIG. 1. As illustrated in FIG. 3, the size of the display covers about 12-40% (and all values and ranges therebetween) of the top surface of the housing 210. The power button 240 and the two arrow or scroll buttons 250, 260 are positioned to the left side of the display 230 as opposed to the bottom of the display 230 as illustrated in FIG. 1. The function of the power button 240 and two arrow or scroll buttons 250, 260 illustrated in FIG. 3 can be the same or different from the function of power button 240 and the two arrow or scroll buttons 250, 260 described above with reference to FIG. 1.

As illustrated in FIG. 3, the display shows the measured pressure in mmHg, the power or charge level of the battery in housing 210, and optionally displays a warning symbol if some type of warning event has occurred (e.g., battery power level too low, malfunction of air pump, malfunction of electronic/processor of motor/pump unit 200, maximum measured/detected pressure exceeded, etc.). As can be appreciated, displays 230 of FIGS. 1 and 3 can display other or additional material (e.g., selected % LOP, operational information for motor/pump unit 200 and/or BFRT cuff 100, LOP pressure, pressure at selected % LOP, operational state or step of the motor/pump unit 200 [e.g., inflating BFRT cuff, obtaining limb LOP, deflating BFRT cuff to selected % LOP, fully deflating BFRT cuff, etc.], manual selection of % LOP, selection of arms or legs for BFRT cuff inflation, select to fully deflate BFRT cuff, time remaining to fully charge the battery, whether the air pump is on/off, etc.).

Operation of BFRT System

The operation of BFRT system 20 illustrated in FIGS. 1-3 will now be described:

Step 1—Turning on or powering up motor/pump unit 200 (if not already turned on). The turning on or powering up of th motor/pump unit 200 can be accomplished by pressing power button 240 on housing 210. If motor/pump unit 200 has been turned off or powered down, motor/pump unit 200 can optionally be configured to calibrate with the ambient pressure when motor/pump unit 200 is tuned on or powered up. Generally, motor/pump unit 200 turning on or powering up of motor/pump unit 200 will cause the display 230 to be turned on.

Step 2—Optionally charge battery in housing 210 of motor/pump unit 200 (if not already sufficiently charged). Generally, the battery in housing 210 should be charged at least 30-50% (and all values and ranges therebetween) of a full charge prior to operation of motor/pump unit 200 to inflate BFRT cuff 100. The battery charge level 292 can be optionally displayed on display 230 of housing 210. In one non-limiting embodiment, the battery in housing 210 should be charged at least 50-100% (and all values and ranges therebetween) of a full charge prior to operation of motor/pump unit 200 to inflate BFRT cuff 100. Motor/pump unit 200 can optionally be configured to cause a warning 294 to be displayed on display 230 of housing 210 when 1) the battery charge level is too low, and/or 2) occlusion has been detected when occlusion was not being tested thereby causing an auto-vent protocol to engage. As can be appreciated, motor/pump unit 200 can be configured such that other or alternative events can cause warning 294 to be displayed on display 230. Motor/pump unit 200 can optionally be configured to prevent operation of the air pump when the battery charge level is too low.

Step 3—Optionally select the limb (e.g., arm or leg) upon which BFRT cuff 100 is to be placed. Motor/pump unit 200 can be optionally programmed such that display 230 on housing 210 requests the user to select using one or both of two arrow or scroll buttons 250, 260 or by touching the display (if the display is a touch screen display) on the limb upon which that BFRT cuff 100 is to be attached during the inflation of BFRT cuff 100. This step and feature of portable motor/pump unit 200 is optional.

Step 4—Place BFRT cuff 100 on the desired limb of the user. The step of placing BFRT cuff 100 on the desired limb of the user can occur at any time prior to motor/pump unit 200 causing BFRT cuff 100 to be inflated. During the step of placing BFRT cuff 100 on the desired limb of the user, proper size BFRT 100 cuff is selected (generally there are different BFRT cuff sizes for the arms and legs), and then BFRT cuff 100 is fitted about the user's limb, and connection strap (e.g., hook and loop fastener strap, etc.) removably secures BFRT cuff 100 to the limb.

Step 5—Select % LOP. Motor/pump unit 200 can be is configured to allow the user to select the desired % LOP to be used during the exercise of the limb. The % LOP can be selected by the user using one or both of two arrow or scroll buttons 250, 260 or by touching the display (if the display is a touch screen display). Motor/pump unit 200 can optionally be configured to not permit a selected % LOP greater than 90%. In one non-limiting embodiment, motor/pump unit 200 allows the user to only select a % LOP from 20-85% and all values and ranges therebetween. Motor/pump unit 200 can optionally provide a suggested % LOP based on the input by the user of the limb upon which BFRT cuff 100 is to be connected. Motor/pump unit 200 can optionally have preprogrammed maximum and/or minimum % LOP values so that a user is optionally unable to selected a % LOP that is greater than the maximum preprogrammed % LOP value and/or the user is optionally unable to selected a % LOP that is less than the minimum preprogrammed % LOP value.

Step 6—Connect motor/pump unit 200 to BFRT cuff 100 prior to activating the pump of the motor/pump unit 200. The step of connecting motor/pump unit 200 to BFRT cuff 100 can occur at any time prior to motor/pump unit 200 causing BFRT cuff 100 to be inflated. As illustrated in FIG. 1, motor/pump unit 200 can be attached to BFRT cuff 100 by the connection of the air tube 270 to air input port 130 of BFRT cuff 100. As can be appreciated, motor/pump unit 200 can be connected to BFRT cuff 100 by other or additional arrangements.

Step 7—Cause air pump of motor/pump unit 200 to activate to cause BFRT cuff 100 to be inflated to the LOP of the limb upon which BFRT cuff 100 is attached. Motor/pump unit 200 can be caused to be activated by the user using one or both of the two arrow or scroll buttons 250, 260 or by touching the display (if the display is a touch screen display), or automatically after the % LOP or selected pressure is selected by the user. Motor/pump unit 200 can optionally be configured to allow the air pump to continue to pump air into BFRT cuff 100 until a maximum preset air pressure is reached in BFRT cuff 100. Motor/pump unit 200 can optionally be configured to stop the operation of the air pump once the maximum preset air pressure is reached in BFRT cuff 100, and thereafter optionally cause BFRT cuff 100 to be partially or fully deflated. Such a feature can be used to reduce or prevent damage to BFRT cuff 100 and/or reduce or prevent harm to the user. Motor/pump unit 200 is configured to terminate the flow of air to BFRT cuff 100 once the LOP in the limb has been detected. The LOP can be measured by use of the oscillometric method by inflating up the BFRT cuff 100 until it senses full occlusion (no arterial pulse) then taking an array average/mean pressure. Motor/pump unit 200 can be configured to sense full occlusion as fast as a half a millisecond such that motor/pump unit 200 can take an average pressure in the span of full occlusion. Thereafter, motor/pump unit 200 is configured to allow or cause air to be removed BFRT cuff 100 until the selected % LOP is reached in BFRT cuff 100. Generally, motor/pump unit 200 is configured to allow or cause air to be removed from BFRT cuff 100 in no more than 10 seconds (e.g., 0.001-10 seconds and all values and ranges therebetween) of motor/pump unit 200 determining or sensing that the LOP has been obtained, and typically motor/pump unit 200 is configured to allow or cause air to be removed from BFRT cuff 100 in no more than 5 seconds of motor/pump unit 200 determining or sensing that the LOP has been obtained, and more typically motor/pump unit 200 is configured to allow or cause air to be removed from BFRT cuff 100 in more than 2 seconds of motor/pump unit 200 determining or sensing that the LOP has been obtained.

The removal of air from BFRT cuff 100 can be by use of a valve in the motor/pump unit 200 that is activated to allow release of air that is flowing from BFRT cuff 100 through air tube 270 and to motor/pump unit 200, and/or the air pump in motor/pump unit 200 can be configured to draw air from BFRT cuff 100 via air tube 270.

Once the % LOP or selected pressure has been obtained in BFRT cuff 100, the air pump terminates operation (if operating) and/or the air release valve in motor/pump unit 200 closes so that no further air is allowed to escape from BFRT cuff 100 after % LOP or selected pressure has been obtained in BFRT cuff 100. Motor/pump unit 200 can optionally be configured to provide a visual signal via display 230 on housing 210 and/or provide an audible sound once the user selected % LOP or selected pressure in BFRT cuff 100 has been obtained.

Step 8—Optionally detach motor/pump unit 200 from BFRT cuff 100 after the % LOP has been obtained in BFRT cuff 100. The detachment of motor/pump unit 200 from BFRT cuff 100 can be accomplished by disconnecting hose connector 280 of air hose 270 from air input port 130 of BFRT cuff 100. As can be appreciated, motor/pump unit 200 can be disconnected from BFRT cuff 100 in other manners. The disconnecting of motor/pump unit 200 from BFRT cuff

100 results in motor/pump unit 200 not regulating the pressure in BFRT 100 cuff while the user exercises a limb while BFRT cuff 100 is connected and partially inflated on the limb.

Step 9—Optionally Auto Regulate pressure in BFRT cuff 100 during use of BFRT cuff 100 by the user. If Auto Regulation is used, motor/pump unit 200 is connected to BFRT cuff 100 during use of BFRT cuff 100 by the user. The Auto Regulation of the pressure of BFRT cuff 100 is used to ensure that proper inflation pressure of BFRT cuff 100 is maintained during the use of BFRT cuff 100.

Step 10—Deflate BFRT cuff 100. The partial or full deflation of BFRT cuff 100 can be accomplished by 1) opening an air release valve on BFRT cuff 100, 2) reconnecting motor/pump unit 200 to BFRT cuff 100 (if not already connected—reconnecting is not required when motor/pump unit 200 remains on BFRT cuff 100 during the use of BFRT cuff 100) and then causing motor/pump unit 200 to cause air to be removed from BFRT cuff 100 (e.g., activating the air pump to cause the air pump to draw air from BFRT cuff 100, and through air tube 270 and then out from housing 210, causing a valve in motor/pump unit 200 to open to allow air to flow from BFRT cuff 100, through air tube 270 and out through the open valve, etc.). The deflation Step includes the optional Intermittent Regulation feature of the BFRT system.

Step 11—Remove BFRT cuff 100 from the user's limb. After the user has completed the exercises for the limb using BFRT cuff 100, the user can remove BFRT cuff 100 from the limb after BFRT cuff 100 has been partially or fully deflated.

The above steps can be modified if the user wishes to perform multiple exercises of the limb using different % LOP. For example, if a user after an exercise wants to continue exercise of the limb but using a different LOP, then after Step 9, the user repeats one or more or Steps 1-3 and 5-10.

Motor/pump unit 200 can optionally be configured to allow a user to select the same % LOP or pressure used on one limb for use on another limb. For example, if a user uses BFRT cuff 100 on his right arm and selected a % LOP of 50% (which was a pressure of 190 mmHg), motor/pump unit 200 can optionally be configured to allow the user to use same BFRT cuff pressure when BFRT cuff 100 is connected to the left arm without having motor/pump unit 200 having to determine the LOP of the left arm. In such an arrangement, motor/pump unit 200 will merely cause BFRT cuff 100 on the left arm to inflate to the same pressure as was used on the right arm. When such a configuration is available on motor/pump unit 200, such option will typically be displayed on display 230 of housing 210.

Figure 4A:
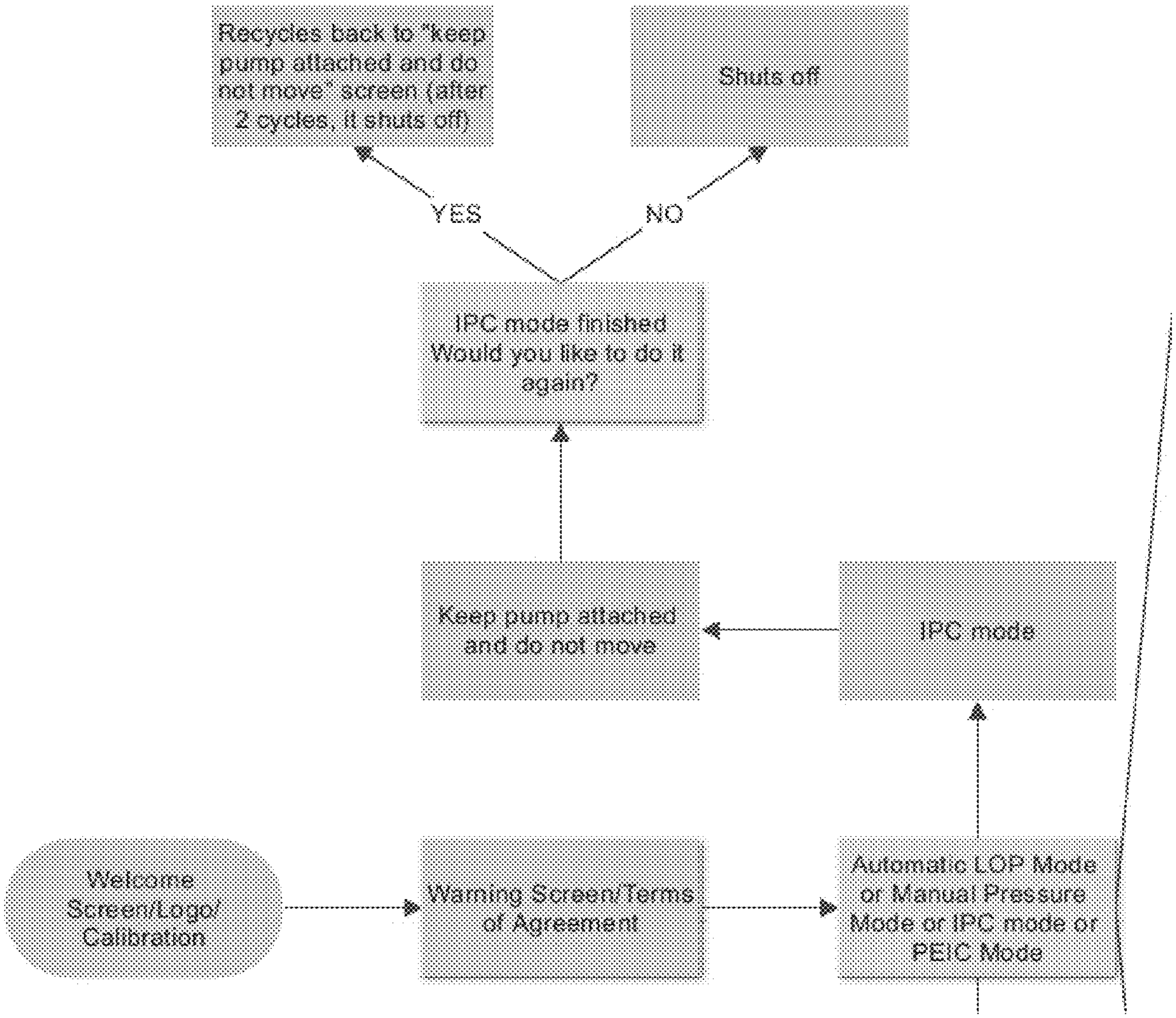
FIGS. 4-12 are illustrations of flow diagrams for the operation of the motor/pump unit and BFRT cuff in accordance with one non-limiting aspect of the present disclosure.
Figure 4B:
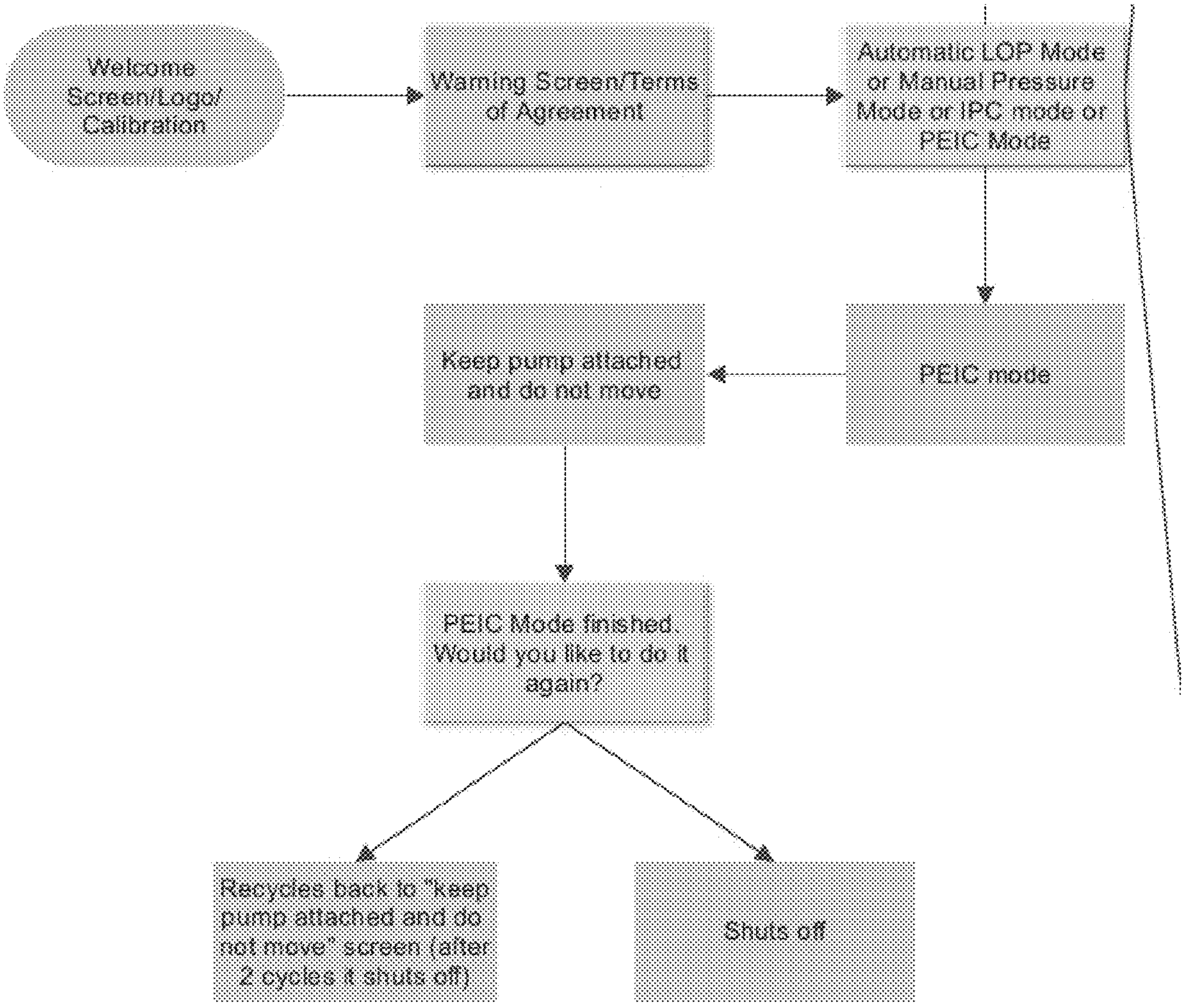

Referring now to FIGS. 4-12, there are illustrations of flow diagrams for the operation of the motor/pump unit 200 and BFRT cuff 100 in accordance with one non-limiting aspect of the present disclosure. FIG. 4 illustrates that the motor/pump unit 200 can operate in either the Automatic LOP mode or the Manual Pressure Mode. As it can be appreciated, the motor/pump unit 200 can be configured to only operate in the Automatic LOP mode or only operate in the Manual Pressure Mode.

Referring again to FIG. 4, after power button 240 is pressed on housing 210 of motor/pump unit 200, an optional Welcome Screen is displayed on display 230. Also, while the Welcome Screen is displayed on display 230, motor/pump unit 200 can optionally be configured to conduct an ambient air pressure calibration with the one or more pressure sensors in housing 210 of motor/pump unit 200.

After the optional Welcome Screen, an optional Warning Screen and/or Terms Of Use Screen can be displayed. One or more buttons 250, 260 may optionally be required to be pressed or display screen 230 touched (when display is a touch screen display) to indicate acknowledgement of the warnings and/or Terms of Use.

After the optional Warning Screen and/or Terms Of Use Screen, if motor/pump unit 200 has more than one mode, then the two or more modes of operation of motor/pump unit 200 can be displayed so that the user can select the mode of operation by use of one or more buttons 250, 260 or by touching display screen 230 (when display is a touch screen display). As illustrated in FIG. 4, motor/pump unit 200 has four (4) operational modes (e.g., Automatic LOP mode, Manual Pressure mode, IPC mode, PEIC mode). FIG. 1 illustrates the operation of the BFRT cuff 100 and motor/pump unit 200 when the IPC mode (Ischemic Preconditioning mode) or PEIC mode (Post Exercise Ischemic Conditioning mode) are selected by the user.

Figure 5A:
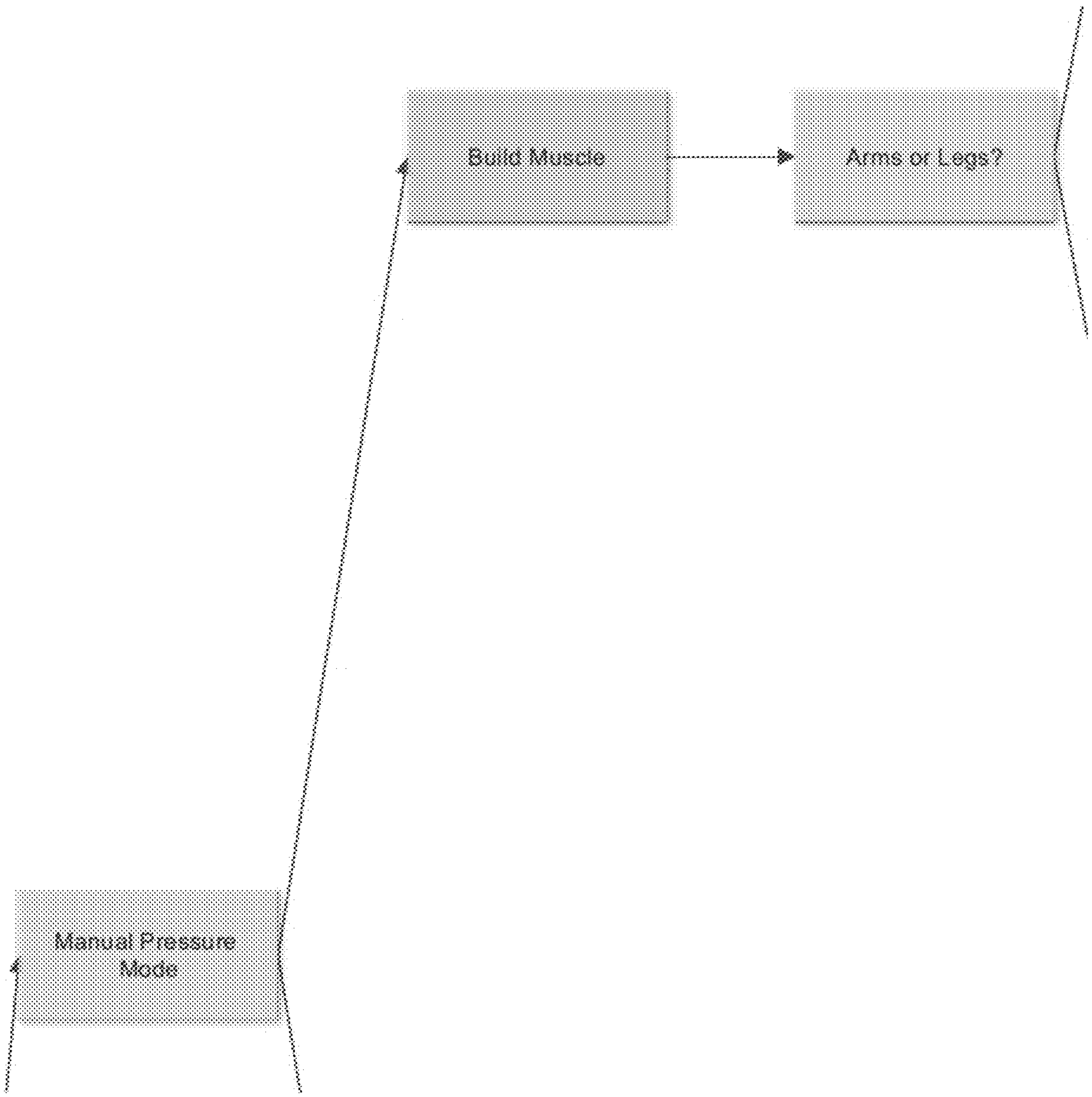
Figure 5B:
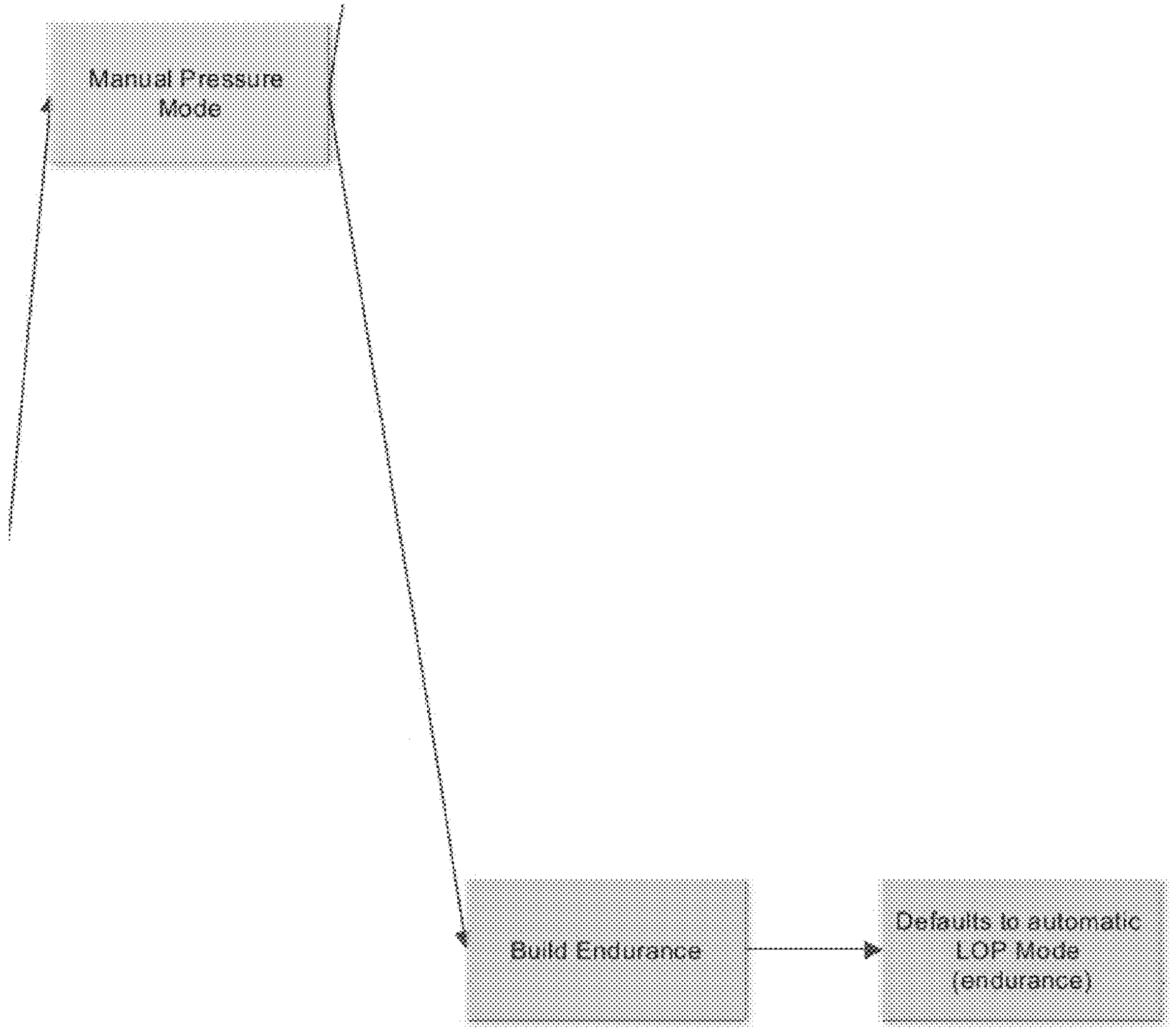
Figure 6A:
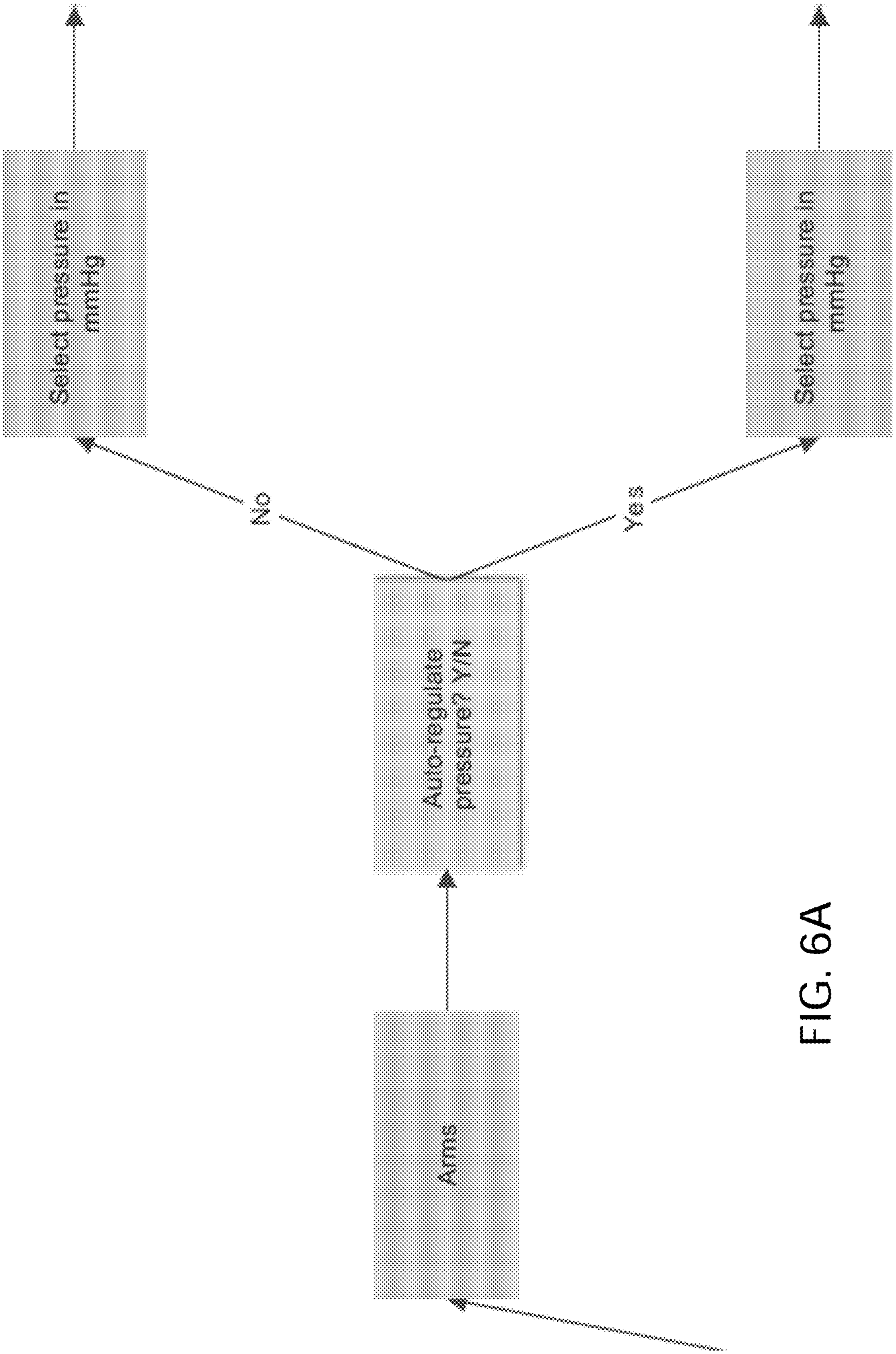
Figure 6B:
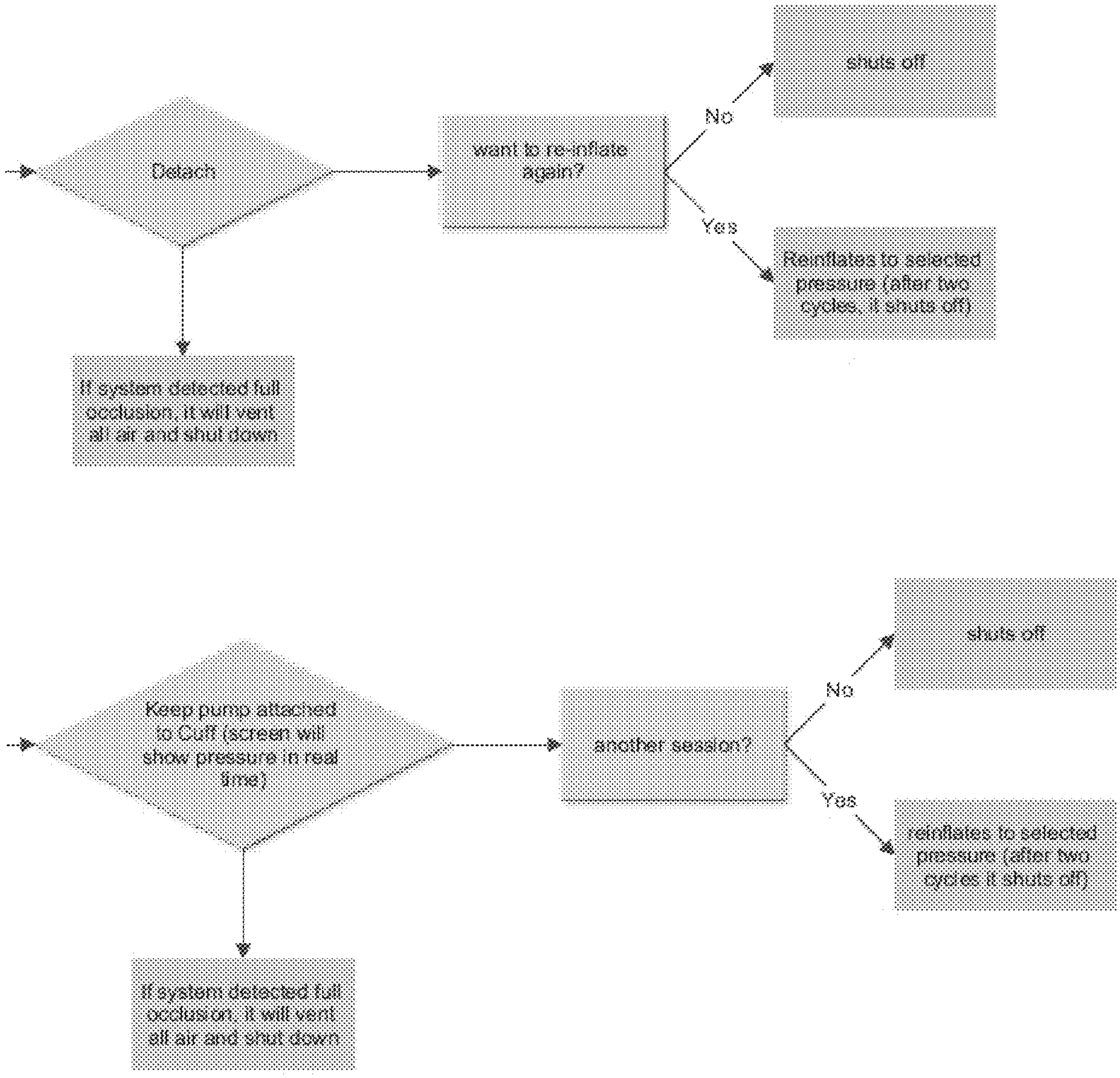
Figure 7A:
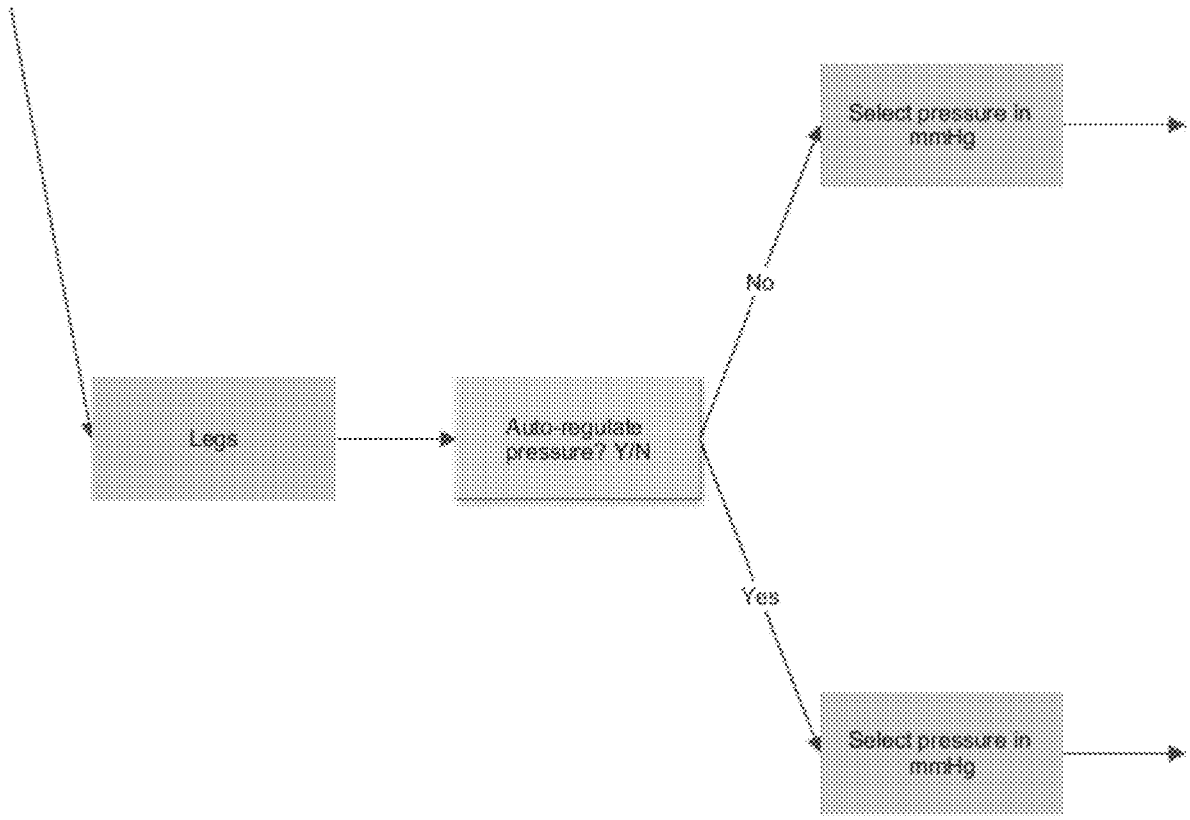
Figure 7B:
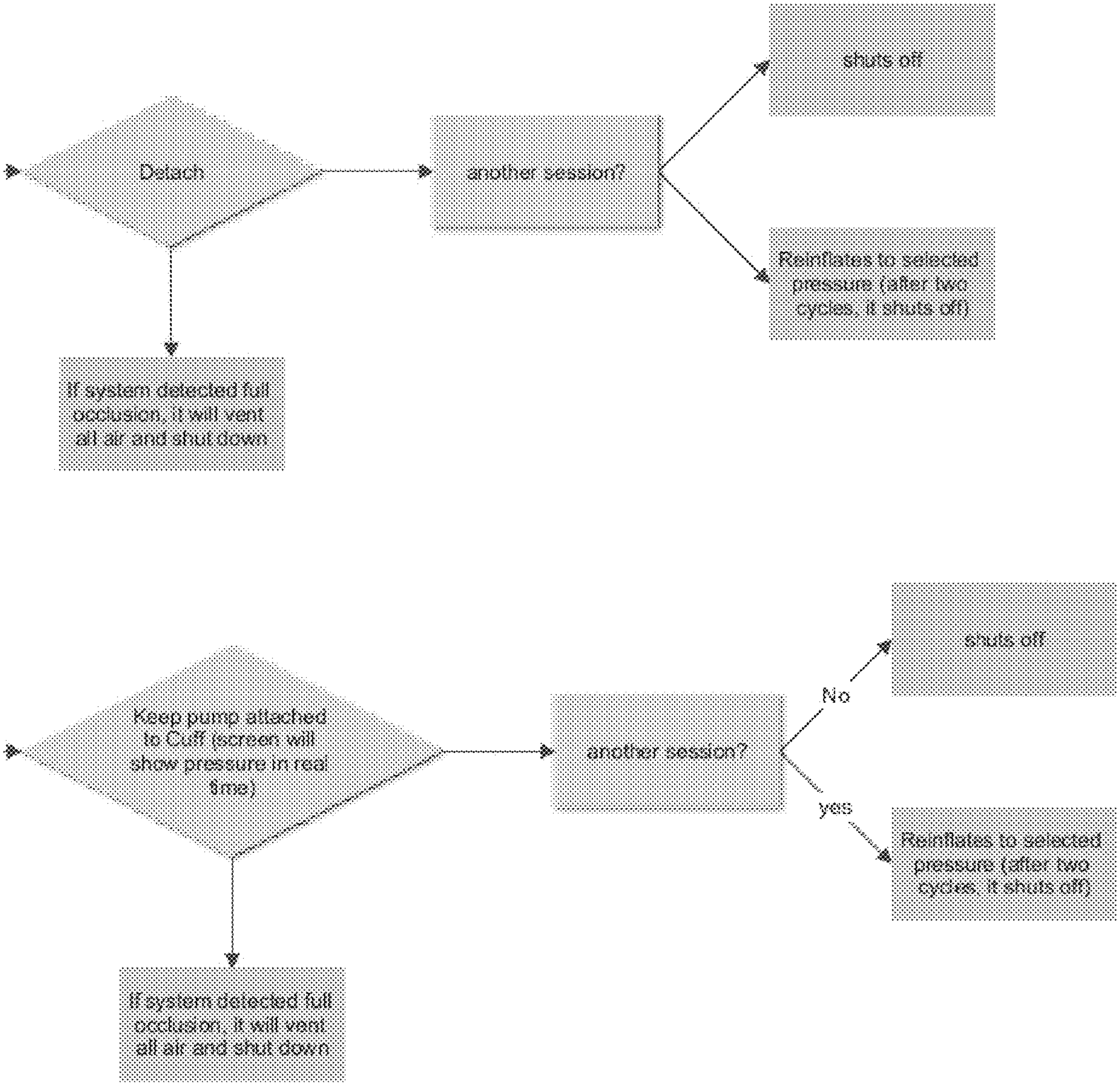

When the Manual Pressure mode is selected by the user, the operation of BFRT cuff 100 and motor/pump unit 200 will follow the operation illustrated in FIGS. 5-7. When motor/pump unit 200 only has a single Manual Pressure Mode or motor/pump unit 200 does not have an Automatic LOP mode and the IPC or PEIC modes are not selected, the operation of BFRT cuff 100 and motor/pump unit 200 can optionally be configured to follow the operation illustrated in FIGS. 5-7 without having the user select another mode.

FIG. 5 illustrates that the user can select between building muscle or building endurance. However, if BFRT cuff 100 and motor/pump unit 200 does not have an Automatic LOP mode, then only the build muscle option can be used by the user. When the build muscle option is selected, the user is optionally asked to select whether the arm or leg is to have BFRT cuff attached thereto. FIG. 6 illustrates the operation of BFRT cuff 100 and motor/pump unit 200 when the arm is selected, and FIG. 7 illustrates the operation of BFRT cuff 100 and motor/pump unit 200 when the leg is selected.

When BFRT cuff 100 and motor/pump unit 200 have an Automatic LOP mode, FIGS. 8-12 illustrated the operation of BFRT cuff 100 and motor/pump unit 200 is such mode.

Figure 8A:
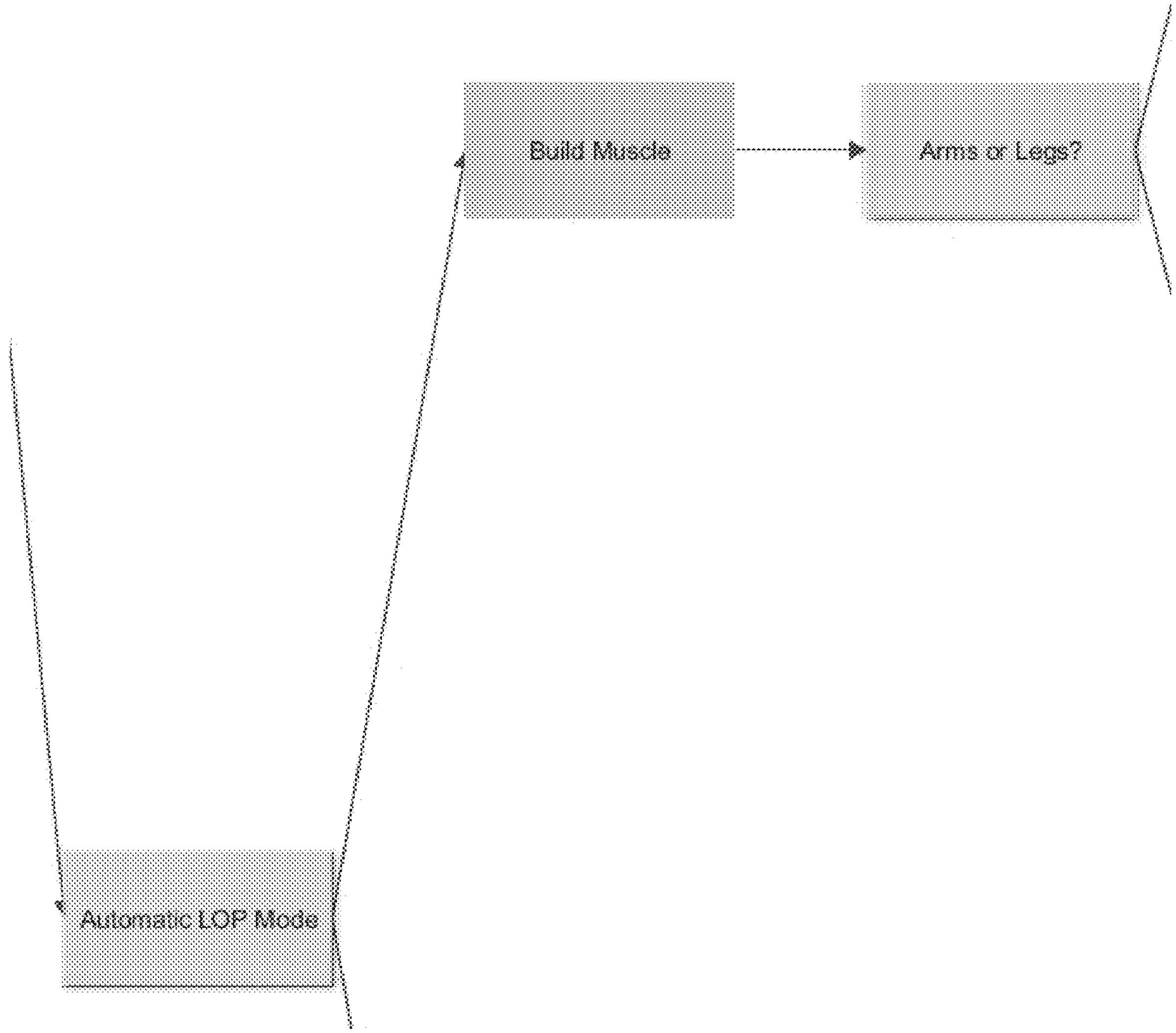
Figure 8B:
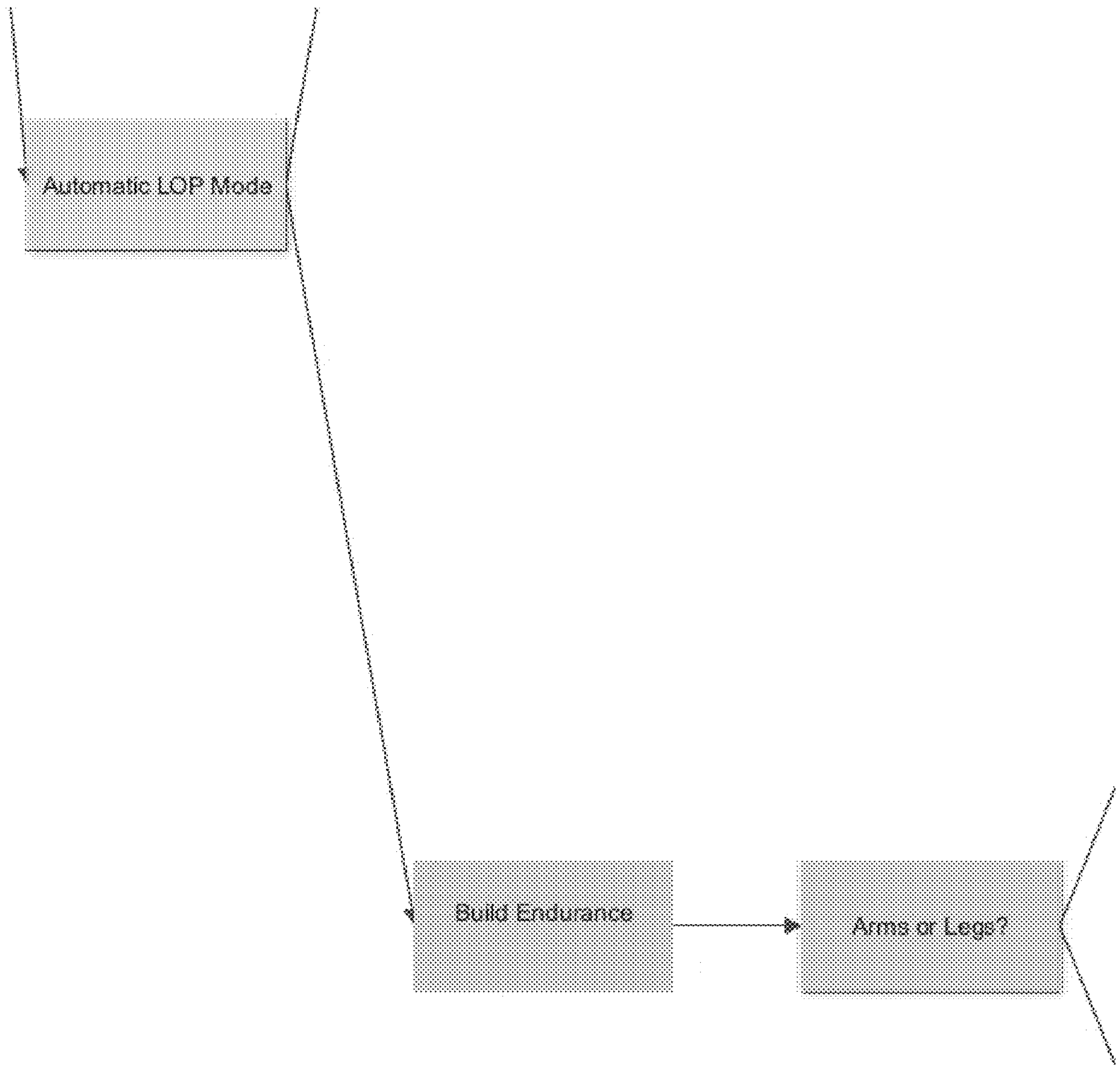
Figure 9A:
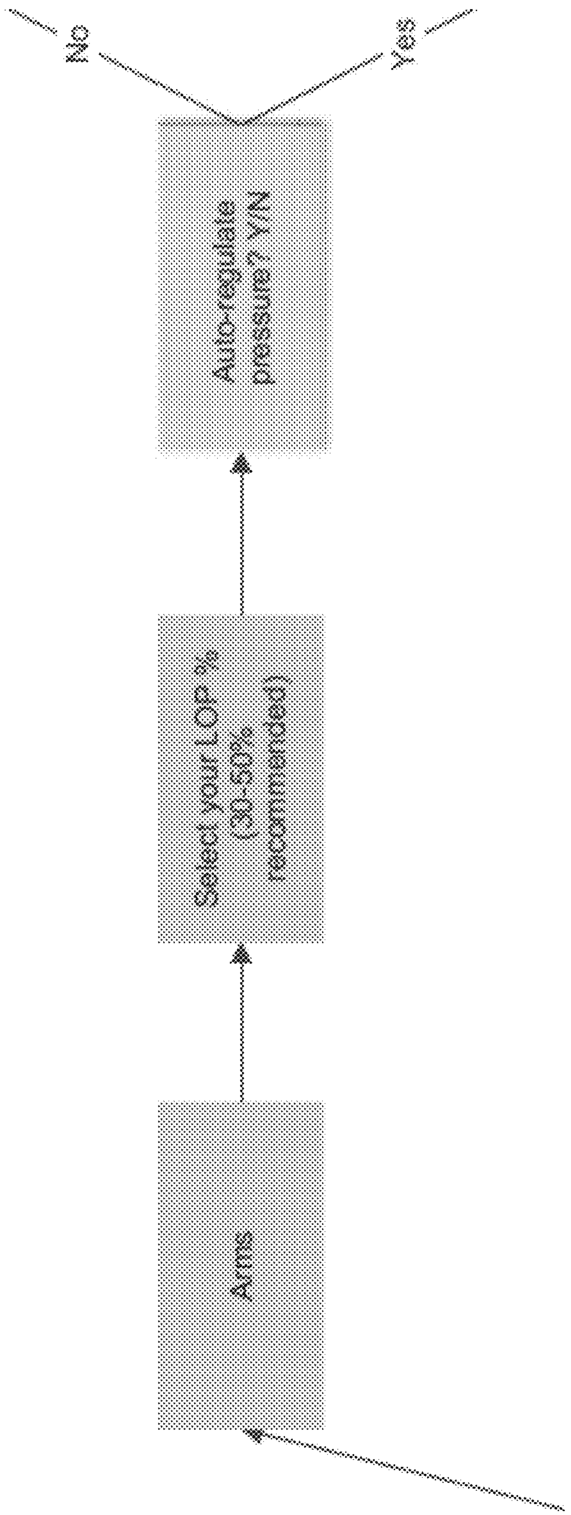
Figure 9B:
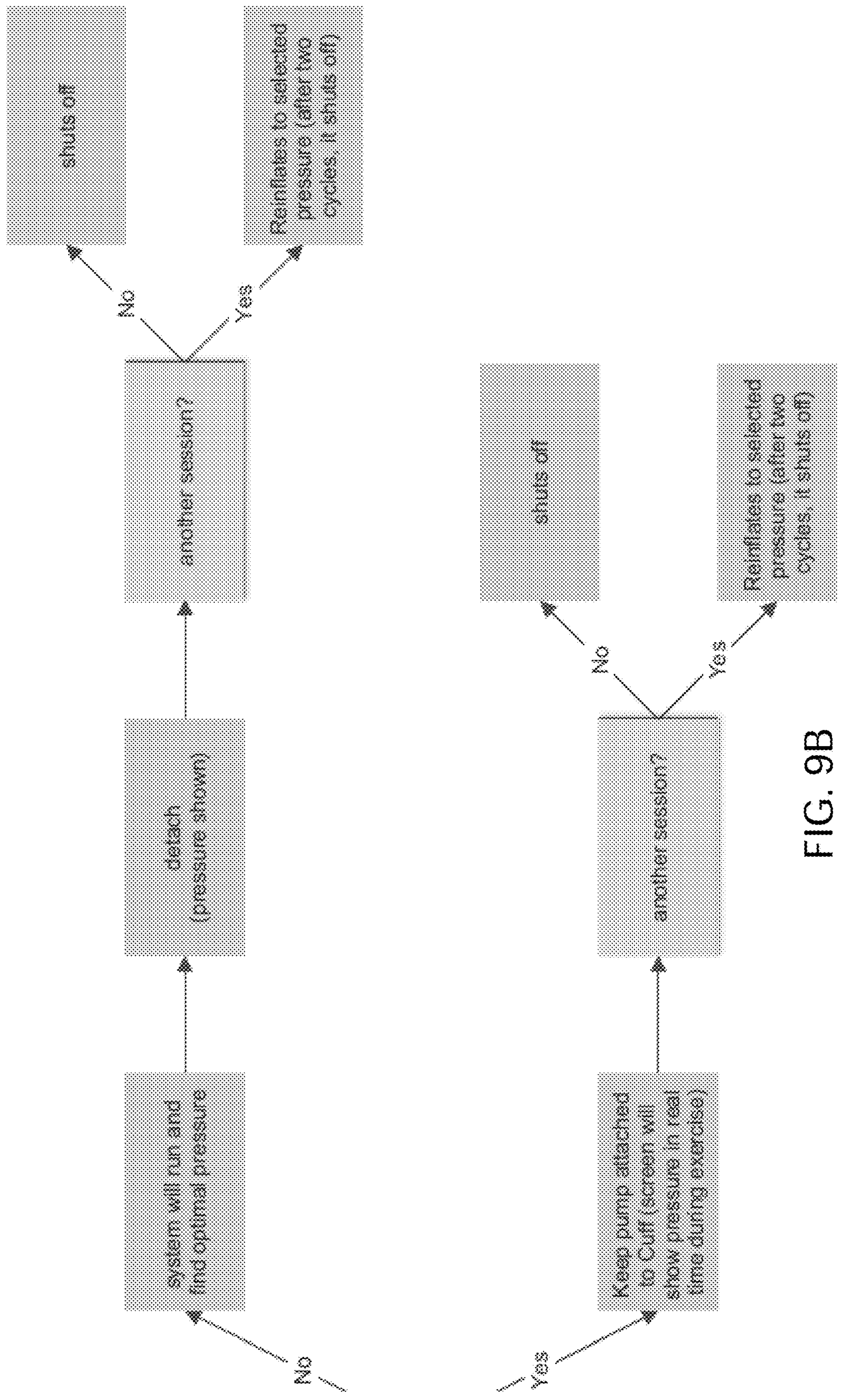
Figure 10A:
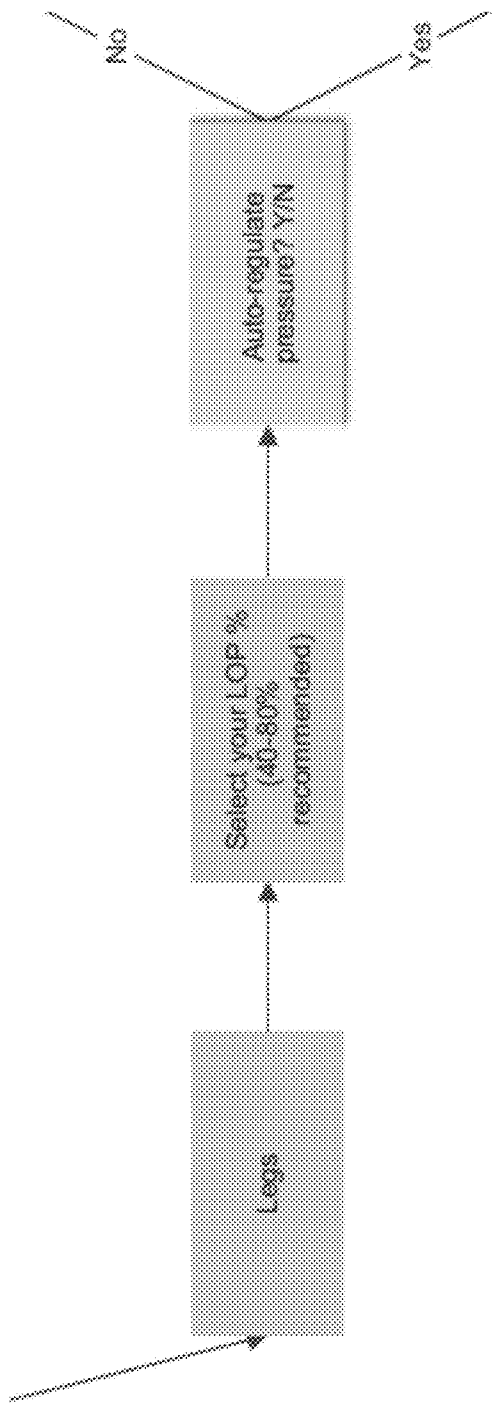
Figure 10B:
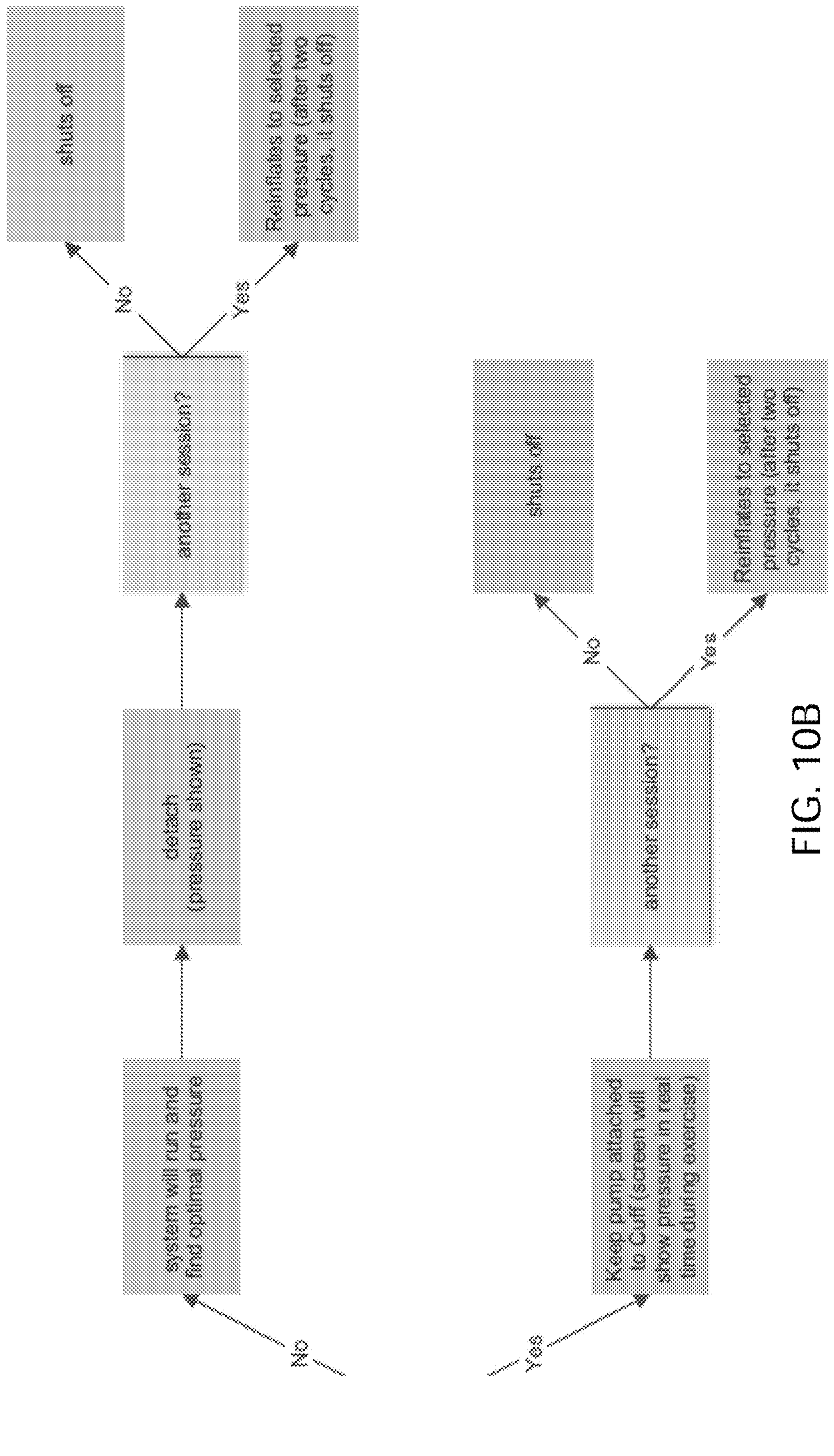
Figure 11:
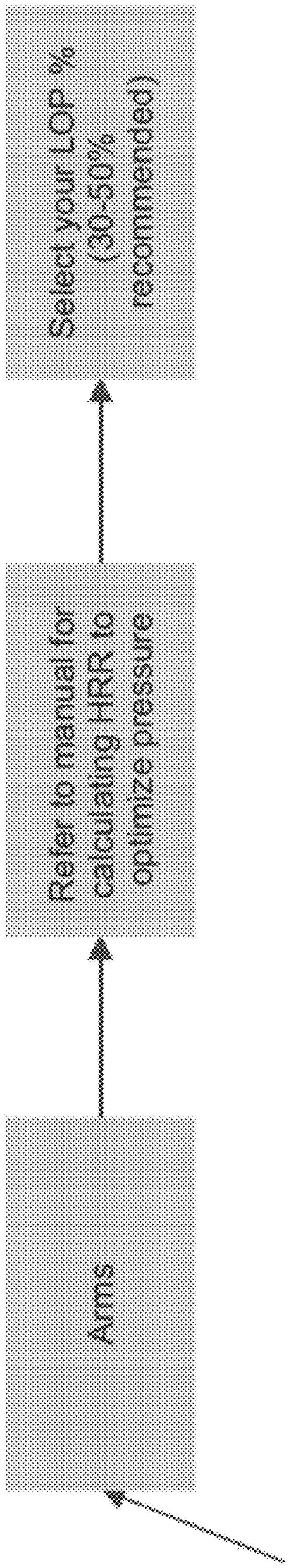
Figure 12A:
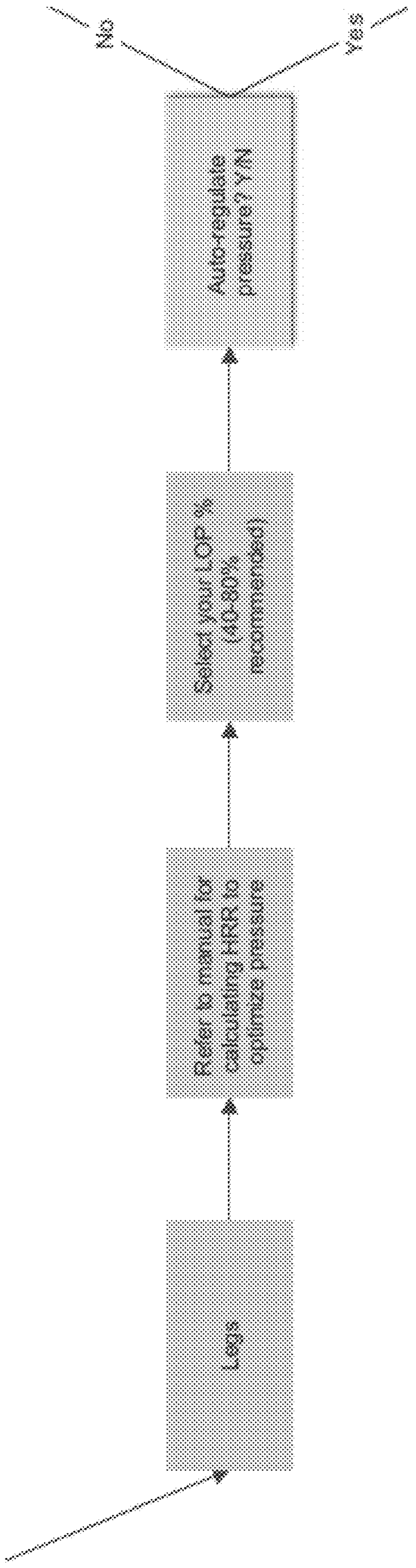
Figure 12B:
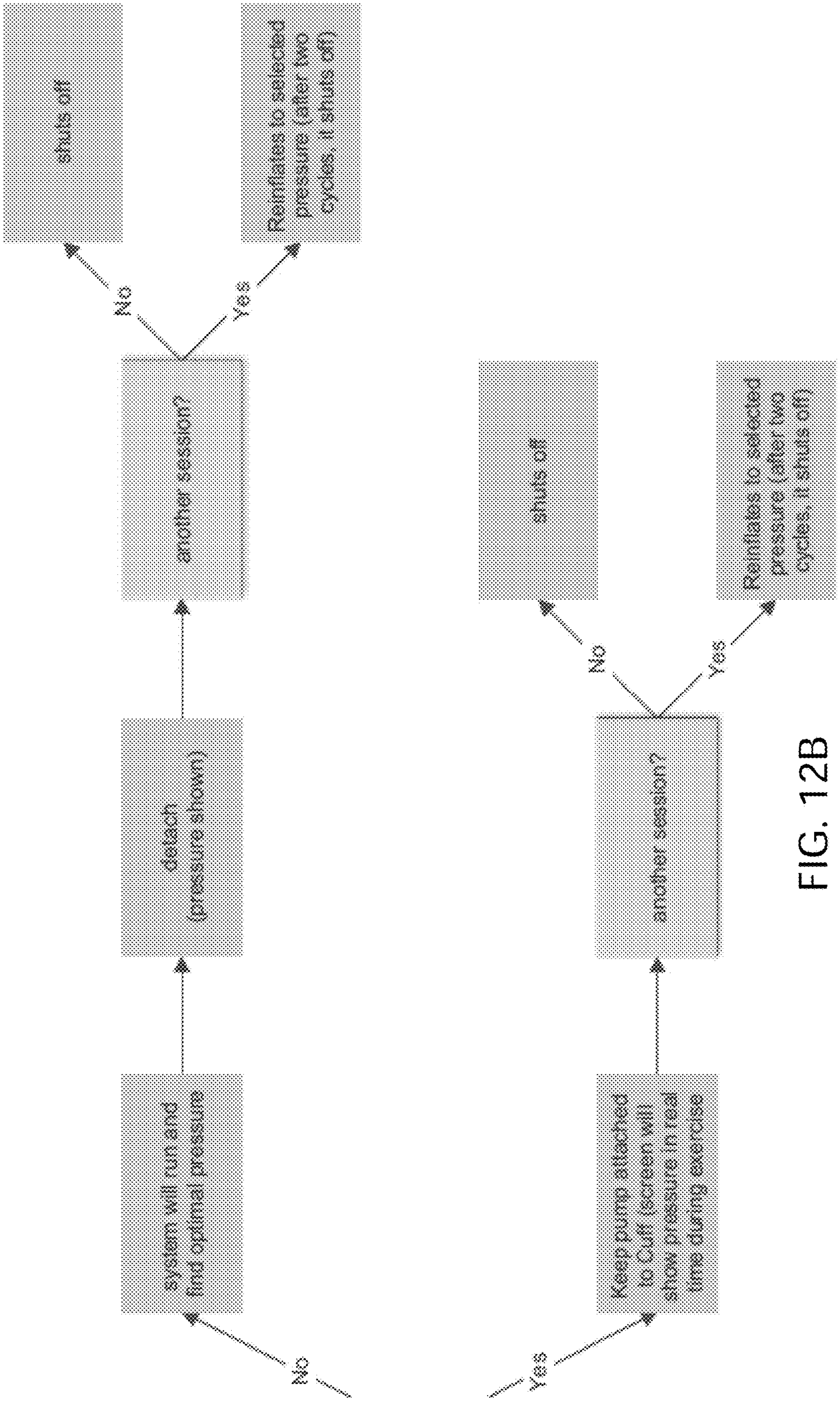
Figure 13:
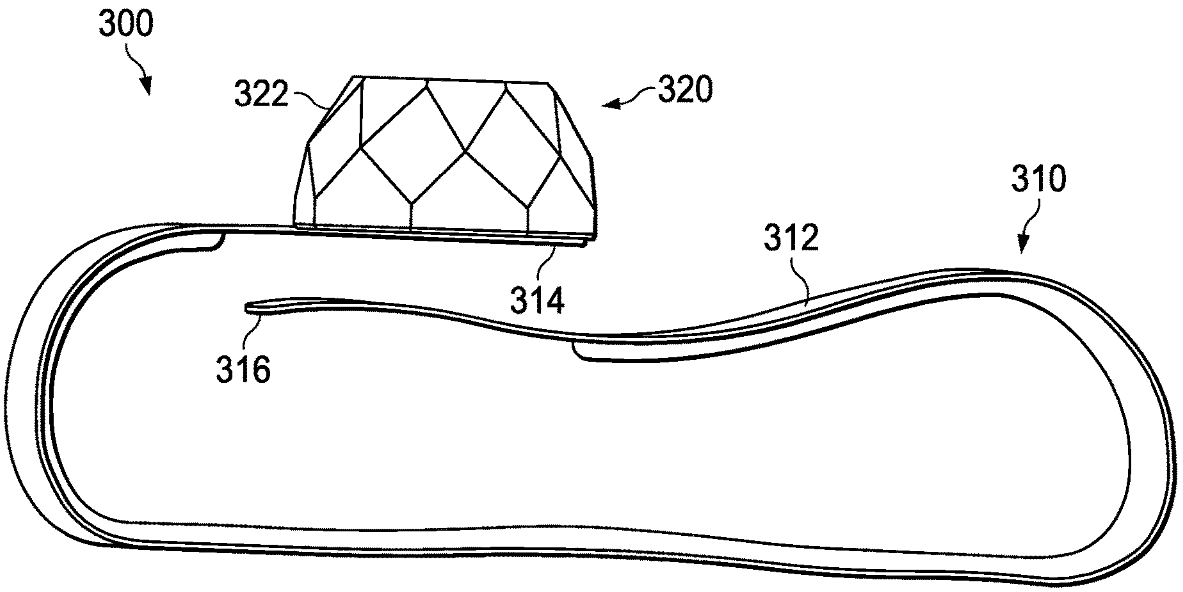
FIG. 13 illustrates a side view of another BFRT cuff system in accordance with the present disclosure that includes a motor/pump unit connected to a portion of the BFRT cuff.

FIG. 8 illustrates that the user can optionally be asked to select the build muscle mode or the build endurance mode. After either mode is selected, the user is then optionally asked to select whether the arm or leg is to have BFRT cuff 100 attached thereto. FIG. 9 illustrates the operation of BFRT cuff 100 and motor/pump unit 200 when the arm is selected in the build muscle mode, FIG. 10 illustrates the operation of BFRT cuff 100 and motor/pump unit 200 when the leg is selected in the build muscle mode. FIG. 11 illustrates the operation of BFRT cuff 100 and motor/pump unit 200 when the arm is selected in the build endurance mode, and FIG. 12 illustrates the operation of BFRT cuff 100 and motor/pump unit 200 when the leg is selected in the build endurance mode.

Referring now to FIGS. 13-17, an alternative non-limiting BFRT system 300 is illustrated that includes a BFRT cuff 310 and motor/pump unit 320.

BFRT cuff 310 includes an inflatable air system formed of at least two layers of material coupled together to create one or more air chambers to be inflated with air and/or some other gas. The inflatable air system is configured in BFRT cuff 310 such that inflation of the inflatable air system produces compression on a target compression zone that in turn produces a restriction of blood flow in the venous system of a user. The BFRT cuff 310 includes an outer material cover 312 having a cavity for containing the inflatable air system so as to isolate the inflatable air system from the skin of the user. The inflatable air system can optionally be secured in the cavity to one or more inner surface of the outer material cover (e.g., stitching, adhesive, melted connection, etc.). The outer material cover 312 is generally made of a flexible and durable material (e.g., nylon, Kevlar™, etc.). In one non-limiting embodiment, outer material cover 312 is formed of an inelastic or non-stretch material. Outer material cover 312 is configured to a) facilitate in distributing the force applied by the inflatable air system to the limb of a user, b) reduce pinching of the user's skin during the inflation of the inflatable air system, and/or c) provide friction between the BFRT and the user's skin to inhibit or prevent rotation of BFRT cuff 310 on the user during use.

BFRT cuff 310 includes one or more air input ports 318 in fluid communication with the inflatable air system to allow a fluid (e.g., air) to flow into and out of motor/pump unit 320. Input port 318 generally includes a valve component. The location of the one or more input ports 318 on BFRT cuff 310 is non-limiting. Generally, at least one input port 318 is located on an outwardly facing surface of outer material cover 312. One or more of input ports 318 is configured to be connected to a motor/pump unit 320. One or more input ports 318 can optionally include a one-way valve (not shown) to prevent undesired deflation of the air inflatable system. The one or more input ports 318 can optionally be configured to allow for manual deflation of the air inflatable system.

As illustrated in FIGS. 13-17, BFRT cuff 310 has a motor/pump unit 320 connected to an outer surface 313 of outer material cover 312. In particular, outer material cover 312 includes a first end 314 and second end 316 and motor/pump unit 320 is connected to a portion of outer material cover 312 that is located closest to first end 314. As can be appreciated, motor/pump unit 320 can be located on any portion of outer material cover 310. Although not shown, the outer material cover 310 is connected to an input port 318 so that motor/pump unit 320 can inflate/deflate the air inflatable system (not shown) that is located in the cavity (not shown) of outer material cover 310.

Motor/pump unit 320 includes a) a housing 322; b) a motor (not shown); c) a pump (not shown); d) one or more displays 324 (e.g., LED screen, OLED screen, etc.) to display measured pressure and/or to display other information; e) optional one or more processors (not shown); f) optional wireless electronics (not shown) that can be used to send/receive wireless signals between the motor/pump unit and a computer, server, data hub, cloud, tablet, smart phone and/or other type of smart device; g) one or more pressure gauges and/or sensors (not shown) used to measure a gas pressure in the air inflatable system; h) optional power source (not shown) to power one or more components of motor/pump unit 320 (e.g., motor, pump, pressure sensor/gauge; electronics, display, etc.); i) optional one or more power ports (not shown) to charge the power source; j) optional connection arrangement 330 to permanently or releasably connect motor/pump unit 320 to outer material cover 310; k) optional one or more fluid connectors 330 to fluidly connect motor/pump unit 320 to the air inflatable system; l) optional GPS system (not shown); m) optional circuit board and other electronics (not shown); n) optional software (not shown); o) optional one or more data ports (e.g., micro USB port, etc.) (not shown) to enable wired transfer of data between motor/pump unit 320 and a computer, server, data hub, cloud, tablet, smart phone and/or other type of smart device; p) optional one or more buttons (e.g., power button, etc.) (not shown), r) optional one or more selection or scroll buttons (not shown) to enable manual operation/control of motor/pump unit 320 and/or to select certain information to be displayed on motor/pump unit 320; s) optional one or more switch(es) (not shown), to enable manual operation/control of motor/pump unit 320; r) optional air hose port (not shown); t) optional one or more lights and/or other indicators (not shown) to indicate a mode and/or operation and/or status of motor/pump unit 320; and u) optional memory (not shown). The shape, size and weight of housing 322 is non-limiting. The material used to form the housing is generally a durable material (e.g., plastic, metal, composite, etc.). The size and weight of motor/pump unit 320 can be the same or similar to motor/pump unit 200 as described above.

As can be appreciated, motor/pump unit 320 can be partially of fully contained within BFRT cuff 310 and/or partially or fully contained within the air inflatable system of BFRT cuff 310. In such an arrangement, motor/pump unit 320 can be partially or fully hidden within BFRT cuff 310. In such an arrangement, outer surface 313 of outer material cover 312 can optionally include one or more displays and/or buttons to display information regarding motor/pump unit 320, display information regarding pressure of the air inflation system, and/or to manually control motor/pump unit 320. As can be appreciated, the one or more displays and/or buttons can be used to display information and/or control motor/pump unit 320 as described above with regard to motor/pump unit 200. In such an arrangement, housing 320 of FIG. 13 merely represents a display 326 and optional buttons on outer surface 313 of outer material cover 312 and some or all of the other components of motor/pump unit 200 are located within the air inflatable system of the BFRT cuff 310.

Figure 14:
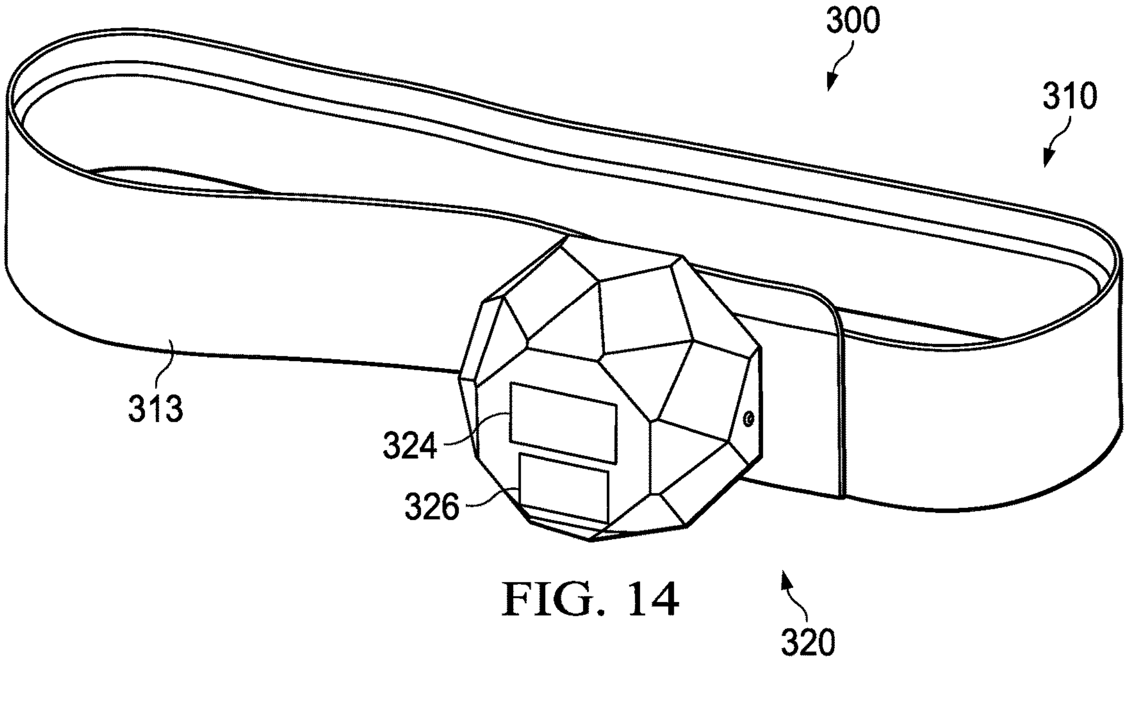
FIG. 14 illustrates a front perspective view of the BFRT cuff system of FIG. 13.

As illustrated in FIG. 14, front surface 324 of motor/pump unit 320 includes a LED display 326 that displays the measured air pressure in the air inflatable system. As can be appreciated, other and/or additional information can be displayed on display 326. The front surface 324 can optionally include one or more buttons and/or switches (not shown).

Figure 15:
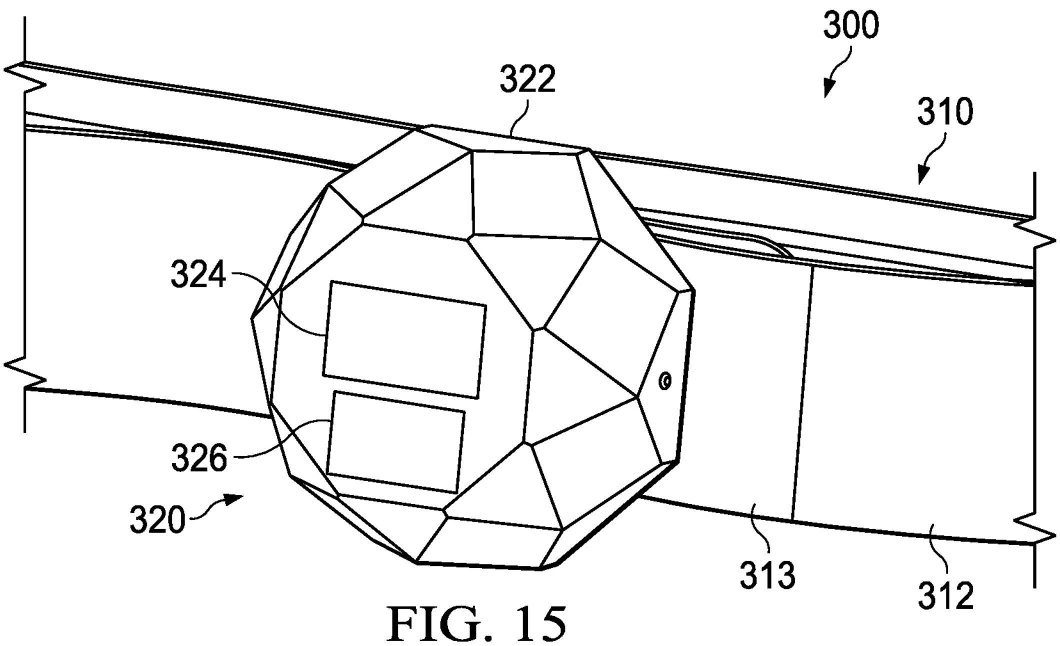
FIG. 15 illustrates an enlarged front perspective view of the BFRT cuff system of FIG. 13.
Figure 16:
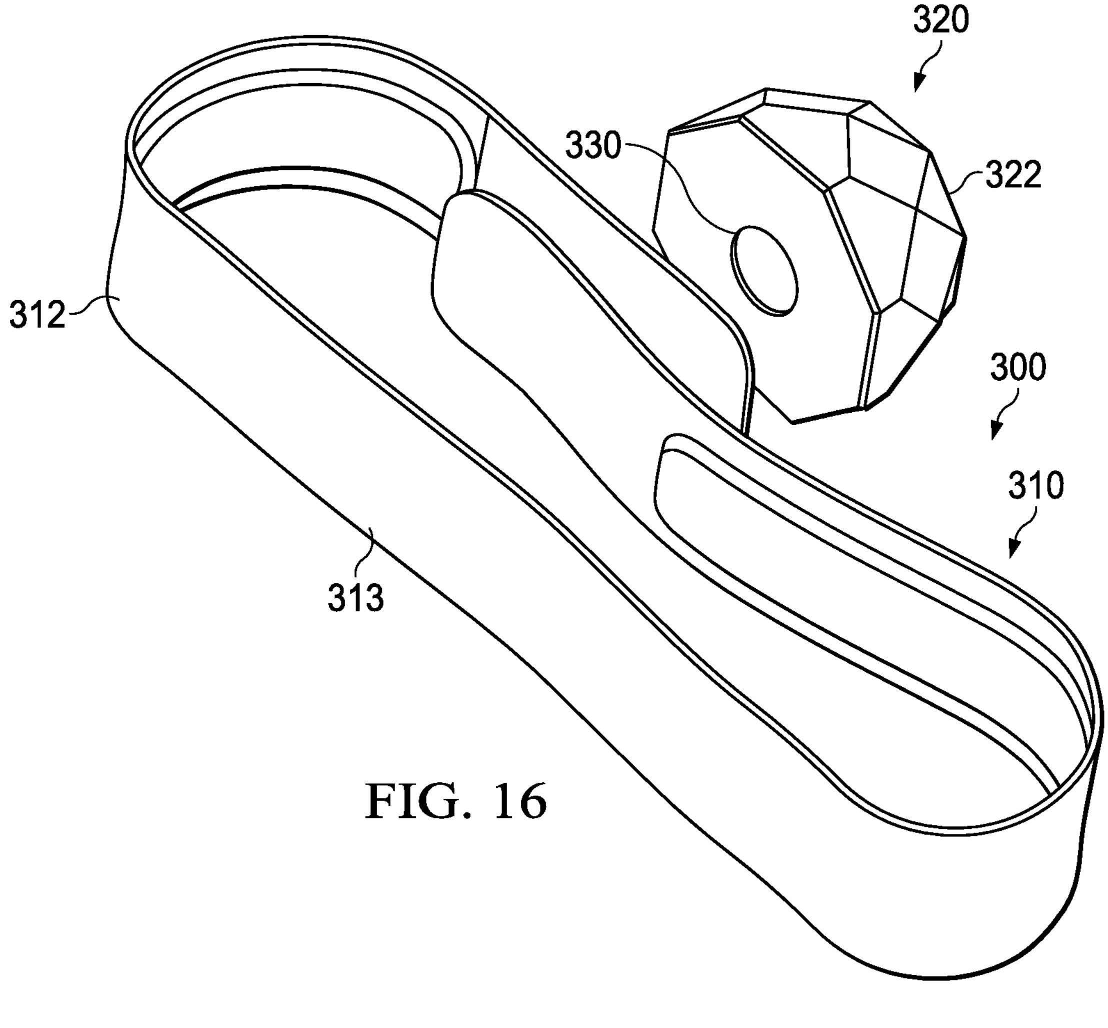
FIG. 16 illustrates a rear perspective view of the BFRT cuff system of FIG. 13 wherein the motor/pump unit is disconnected from the BFRT cuff.
Figure 17:
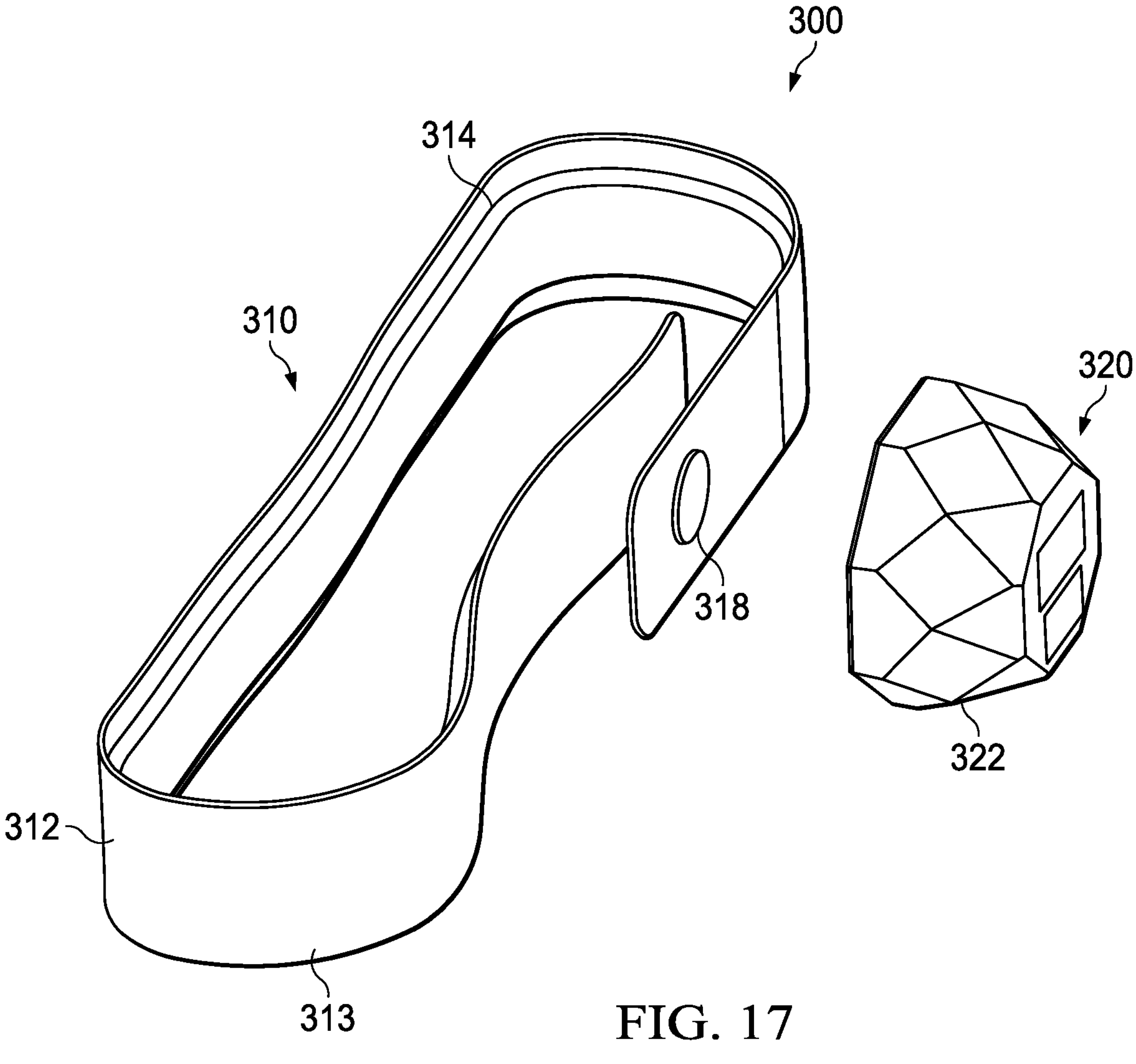
FIG. 17 illustrates a top perspective view of the BFRT cuff system of FIG. 16.

Referring now to FIGS. 15-16, motor/pump unit 320 is illustrated as being releasably connectable to outer surface 313 of outer material cover 312 of BFRT cuff 310. The type of connection arrangement is non-limiting (e.g., snap connection arrangement, hook and loop fastener, slot connection arrangement, tongue and groove connector, etc.). As illustrated in FIG. 17, outer surface 313 of outer material cover 312 of BFRT cuff 310 includes a connector 318 configured to releasably connect to housing 322 of motor/pump unit 320.

BFRT cuff 310 includes a cuff fastening arrangement (not shown) to releasably secure BFRT cuff 310 to a user. The type of fastening arrangement is non-limiting (e.g., snap connection arrangement, hook and loop fastener, snap fastener, button fastener, etc.).

Operation of BFRT System

The operation of BFRT system 300 can be the same of similar to the operation as described above with regard to BFRT system 20.

Another non-limiting operation sequence of BFRT system 300 is set forth below. It will be understood that one or more steps described above with regard to BFRT system 20 can be used with the one or more step of BFRT system 300 described below.

In the first step, a user (not shown) selects an appropriate size of BFRT cuff 310 based on the user's upper arm girth if exercising the upper limbs, or upper thigh girth if exercising the lower limbs.

In the next step, the user applies BFRT cuff 310 about his/her arm or leg and secures BFRT cuff 310 in the desired position on his/her arm or leg. Motor/pump unit 320 should be connected to BFRT cuff 310 prior to attempting to inflate the air inflatable system of BFRT cuff 310. In some non-limiting embodiments, motor/pump unit 320 is integrated in BFRT cuff 310, thus does not need to be connected to BFRT cuff 310.

The next step is to inflate the air inflatable system in BFRT cuff 310. This can be accomplished by manually activating motor/pump unit 320, or by wirelessly activating motor/pump unit 320. Such wireless activation can be accomplished by using a mobile app or program on a smart device (e.g., smart phone, tablet, computer, laptop computer, server, data hub, cloud, etc.) and the like. As can be appreciated, a smart device and the like can also or alternatively be wired connected to motor/pump unit 320 or BFRT cuff 310 (when motor/pump unit 320 is integrated in BFRT cuff 310).

The pump in motor/pump unit 320 injects air into the air inflatable system in BFRT cuff 310 until a desired pressure is reached. The pressure in the air inflatable system can be optionally viewed on display 324 on housing 322 of motor/pump unit 320 and/or on another device (e.g., smart phone, computer, tablet, etc.). BFRT cuff 310 can optionally include a pressure limiting valve (not shown) to prevent over pressurization of the air inflatable system. Once the desired pressure is achieved in the air inflatable system, the operation of the pump is terminated. Thereafter, the user can proceed to exercise.

During exercise, the BFRT system can include an Auto Regulation Feature whereby if the pressure sensor determines that the pressure in the air inflatable system has exceed a predetermined pressure, air pressure can be released from the air inflatable system until the predetermined pressure in the air inflatable system is obtained. If the pressure sensor determines that the pressure in the air inflatable system is below a predetermined pressure, air pressure can be increased in the air inflatable system by activating motor/pump unit 320 until the predetermined pressure in the air inflatable system is obtained. The increase/decrease in pressure in the air inflatable system can occur during the use of BFRT cuff 310 without requiring the user to interrupt his/her exercise. Such a feature is a significant improvement over prior art BFRT arrangements wherein a user needed to stop exercising to manually increase or decrease the air pressure in the BFRT arrangement.

As illustrated in FIGS. 16-17, motor/pump unit 320 can be configured to be removable from BFRT cuff 310. If motor/pump unit 320 is removed from BFRT cuff 310 after the air inflatable system has been inflated, BFRT cuff 310 typically includes a valve arrangement that prevents deflation of the air inflatable system during and after the removal of motor/pump unit 320 from BFRT cuff 310.

When the user is through with the desired exercises, the user may manually release the pressure in the air inflatable system, use an app or program on a computer or other type of smart device to deflate the air inflatable system, and/or the air inflatable system can be automatically deflated. Thereafter, the user can remove BFRT cuff 310 from his/her arm or leg.

As can be appreciated, many of the steps of operation of BFRT cuff 310 can be the same or similar to the steps of operation of BFRT cuff 100 as described above.

BFRT cuff 310 of the present disclosure includes several unique features as discussed in more detail below.

BFRT cuff 310 can have a urethane-coated air bladder. The urethane coating on the bladder adds to patient comfort by reducing pinching of the skin by the bladder when inflated.

BFRT cuff 310 includes a motor/pump unit 320 to inflate/deflate the one or more air chambers in BFRT cuff 310, and which motor/pump unit 320 is detachable connectable to BFRT cuff 310 and can remain connected to BFRT cuff or be removed from the BFRT cuff prior to, during, and/or after use of BFRT cuff 310. When motor/pump unit 320 remains on BFRT cuff 310 while the user exercises, motor/pump unit 320 can be configured to automatically activate to reduce or increase air pressure in the air inflatable system so as to maintain a desired air pressure in the air inflatable system during the exercise routine. Alternatively, the user can manually activate motor/pump unit 320 to increase/decrease the pressure in the air inflatable system. Motor/pump unit 320 can be removed from BFRT cuff motor/pump unit 320 to reduce the weight of BFRT system 300 on the user during exercise or to prevent inadvertent damage to motor/pump unit 320 during rigorous exercise. Motor/pump unit 320 can be connected to and detached from BFRT cuff 310 at any time prior to, during, or after an exercise routine. BFRT cuff 310 includes a valve arrangement that prevents undesired deflation of the air inflatable system during the connection and detachment of motor/pump unit 320 to/from BFRT cuff 310.

Motor/pump unit 320 can be powered by a battery contained in the housing of motor/pump unit 320. Such a feature eliminates the need for power cords to operate motor/pump unit 320, thus providing more flexibility and ease of use of BFRT cuff 310. The battery can be rechargeable and housing 322 of motor/pump unit 320 can optionally include a power port so that a power cord, USB cord, etc. can be connected to housing 322 to recharge the battery. As can be appreciated, motor/pump unit 320 can be designed to allow for wireless charging of the battery.

Motor/pump unit 320 used with BFRT cuff 310 can include one or more displays 324. These one or more displays 324 can be used to inform a user of a) whether the pump is on/off, b) battery status, c) pressure level for pressure in the one or more air chambers of BFRT cuff 310, d) time/date, e) whether pressure in the one of more air chambers of BFRT cuff 310 is at or below limb occlusion pressure, f) error notification/status, g) security status (e.g., locked, unlocked, etc.), h) ambient temperature, i) timer/clock information, j) alarm status/notification, k) time of use, l) pressure mode, operation mode, and/or selected training session, m) whether full occlusion has been obtained, n) whether maximum workout time period has occurred, and/or o) wireless connection status to computer, tablet, smart phone, and/or other type of smart device.

Motor/pump unit 320 on BFRT cuff 310 can be configured to be manually controlled by the user activating/pressing/moving buttons, switches, locations on the display, etc., and/or motor/pump unit 320 can be configured to be controlled wirelessly and/or wired by a computer, tablet, smart phone, and/or other type of smart device. The wired and/or wireless control of motor/pump unit 320 can be accomplished via a program or app running on a computer, tablet, smart phone, and/or other type of smart device. Wired and/or wireless control of motor/pump unit 320 can also be accomplished by voice commands. As can be appreciated, motor/pump unit 320 can include electronics, software, etc. to enable voice control of motor/pump unit 320 without the need of a computer or other type of smart device. When programs or apps are used to wire and/or wirelessly control motor/pump unit 320, these programs or apps can be used to both monitor the operation of motor/pump unit 320 as well as control the operation of motor/pump unit 320 and/or monitor the status of BFRT cuff 310.

BFRT cuff 310 can optionally include a pressure sensor and one or more processors to a) facilitate in controlling/maintaining/regulating the pressure in the one or more air chambers of BFRT cuff 310, b) provide pressure information to motor/pump unit 320 to be displayed on motor/pump unit 320 and/or wired and/or wirelessly sent to a remote device, c) provide pressure information to be displayed on one or more displays on BFRT cuff 310 and/or wired and/or wirelessly sent to a remote device, d) provide pressure information wirelessly to a computer, tablet, smart phone, and/or other type of smart device and have such information displayed using a computer program or mobile app. The one or more pressure sensors can be part of the motor/pump unit 320 and/or be located at a different location on BFRT cuff 310.

Motor/pump unit 320 on BFRT cuff 310 can be configured to allow a user to manually input a predetermined limb occlusion pressure; motor/pump unit 320 uses such information to control/maintain/regulate the pressure in the one or more air chambers of BFRT cuff 310. BFRT cuff 310 can also or alternatively be configured to wired and/or wirelessly receive information regarding the automatic calculation of a predetermined limb occlusion pressure via a computer program or mobile app running on a computer, tablet, smart phone, and/or other type of smart device and to then use such information to control/maintain/regulate the pressure in the one or more air chambers of BFRT cuff 310.

BFRT cuff 310 can include one or more sensors and/or control systems to automatically shut off the pump and/or release pressure in the one or more air chambers of BFRT cuff 310 after sensing that an occlusion pressure in the one or more air chambers has been maintained for some preset period of time (e.g., 0.001-30 seconds, 0.001 seconds to 1 minute, 0.001 seconds to 4 minutes, 0.001 seconds to 5 minutes, etc.). In one non-limiting arrangement, BFRT cuff 310 and/or motor/pump unit 320 can include one or more sensors and/or control systems to automatically shut off the pump and/or release pressure in the one or more air chambers of BFRT cuff 310 after sensing that an occlusion pressure in the one or more air chambers has been maintained for 0.001 seconds to 45 seconds (and all values and ranges therebetween). Such a feature facilitates in the proper use of BFRT cuff 310 and prevents extended periods of time of occlusion pressure being applied to user so as to not damage or impair rehabilitation of the tissue of the user during the use of BFRT cuff 310.

BFRT cuff 310 and/or motor/pump unit 320 can include a sensor and/or control system to automatically shut off the motor/pump unit and/or to release pressure in the one or more air chambers of BFRT cuff 310 after some preset period of time (e.g., 20 minutes, etc.). Such a feature preserves the life of BFRT cuff 310 and functions as another safety feature of BFRT cuff 310. In one non-limiting arrangement, BFRT cuff 310 and/or motor/pump unit 320 include one or more sensors and/or control systems to automatically shut off pump and/or motor/pump unit 320, and/or to release pressure in the one or more air chambers of BFRT cuff 310 after 2-20 minutes (and all values and ranges therebetween).

BFRT cuff 310 and/or motor/pump unit 320 can include one or more sensors to detect use and non-use of BFRT cuff 310 (e.g., motion sensor, etc.) and to automatically shut off the pump and/or releases pressure in the one or more air chambers of BFRT cuff 310 after some preset period of time of non-use of BFRT cuff 310 (e.g., 1-20 minutes, etc.). Such a feature preserves the life of BFRT cuff 310. In one non-limiting arrangement, BFRT cuff 310 and/or motor/pump unit 320 include one or more sensors to detect use and non-use of BFRT cuff 310 and to automatically shut off the pump and/or releases pressure in the one or more air chambers of BFRT cuff 310 after 1-10 minutes (and all values and ranges therebetween) of non-use of BFRT cuff 310.

BFRT cuff 310 can optionally include a GPS sensor or other type of location sensor. This type of sensor is used to track the location of BFRT cuff 310 and/or to monitor movement of BFRT cuff 310 during an exercise routine to determine if proper use of BFRT cuff 310 is being utilized by the user during a certain exercise routine.

BFRT cuff 310 can optionally include one or more lateral sensors, movement sensors and/or a gyroscope arrangement to monitor movement of BFRT cuff 310 during an exercise routine to determine if proper use of BFRT cuff 310 is being utilized by the user during a certain exercise routine.

BFRT cuff 310 can include one or more pressure modes (e.g., ischemic preconditioning mode ("IPC"), manual mode, auto mode, etc.). These modes can be manually selected, wirelessly selected, wire selected, and/or selected by voice command. The IPC mode is a mode in which BFRT cuff 310 is inflated to full occlusion of the artery for some time period (e.g., 10 seconds-5 minutes [and all values and ranges therebetween], etc.) and at some rest period interval (e.g., 10 seconds-4 minutes [and all values and ranges therebetween], etc.) between the periods of full occlusion. In auto mode, motor/pump unit 320 automatically sets the optimal pressure based on what LOP % set by the user or by information wirelessly received from a device that has automatically calculated the pressure optimal pressure based on what LOP % that is set by the user. In the manual mode, the user manually sets the pressures on BFRT cuff 310 or on a device that then wired and/or wirelessly sends the pressure information to BFRT cuff 310.

BFRT cuff 310 can be monitored and/or controlled by a computer program and/or mobile app running on a computer, tablet, smart phone, and/or other type of smart device. The computer program and/or mobile app can 1) select a mode of operation for BFRT cuff 310, 2) activate/deactivate BFRT cuff 310, 3) transmit/receive information to/from BFRT cuff 310, 4) select/control/maintain/reduce the pressure in the one or more air chambers of BFRT cuff 310 while the user uses BFRT cuff 310, 5) monitor the operation of BFRT cuff 310, 6) maintain a log regarding the use of BFRT cuff 310, 7) provide an exercise plan for a user that is using BFRT cuff 310, 8) record/monitor the progress/compliance of a user's exercise plan, 9) select/recommend a BFRT training session for a user, 10) keep track of a user's BFRT training sessions, 10) provide suggested training tips for BFRT to the user, 11) provide BFRT information to a user, 12) transmit/receive data to/from a user's BFRT trainer or instructor, 13) maintained a pressure or pressure range or % LOP or range of % LOP in the BFRT cuff during use, and/or 14) partially or fully deflate the BFRT cuff for a certain period of time after an exercise is completed, between exercise routines, or after non-use of the BFRT cuff is detected.

BFRT cuff 310 can include security protocols to prevent misuse and/or unauthorized use of BFRT cuff 310. A computer program or mobile app that can run on a computer, tablet, smart phone, and/or other type of smart device can include password protection and/or other security controls to prevent unauthorized use of BFRT cuff 310 and/or access to personal information regarding the use of BFRT cuff 310. The motor/pump unit 320 can also include password protection to prevent unauthorized operation of BFRT cuff 310.

To aid the Patent Office and any readers of this application and any resulting patent in interpreting the claims appended hereto, Applicant does not intend any of the appended claims or claim elements to invoke 35 U.S.C. 112(f) unless the words "means for" or "step for" are explicitly used in the particular claim.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall there between. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

What is claimed:

1. A method for exercising using a blood flow restriction training (BFRT) system comprising:

a. providing a portable BFRT cuff; said portable BFRT cuff includes i) a flexible outer material, ii) a single air chamber that is encapsulated by said flexible outer material, and iii) a connection arrangement that is configured to releasably secure said portable BFRT cuff to a limb of a user;

b. providing a portable inflation unit; said portable inflation unit is configured to at least partially inflate said portable BFRT cuff during operation of said portable inflation unit; said portable inflation unit includes a housing, a fluid pump, a pressure sensor, a controller, a wireless receiver, a rechargeable power source and an air connection arrangement; said fluid pump, said pressure sensor, said controller, said wireless receiver, and said rechargeable power source are contained within said housing; said housing is releasably connectable to said portable BFRT cuff, said housing has a size that is less than 400 cubic inches and a weight that is less than 4 lbs.; said controller is configured to control an operation of said fluid pump to a) cause said fluid pump to pump fluid into said portable BFRT cuff to inflate said portable BFRT cuff and b) cause said fluid pump to remove fluid from said portable BFRT cuff, said air connection arrangement is located on a bottom surface of said housing and is configured to fluidly connect said fluid pump to said portable BFRT cuff when said housing is releasably connected to said portable BFRT cuff, said housing of said portable inflation unit connected to said portable BFRT cuff to enable fluid flow between said portable BFRT cuff and said portable inflation unit;

c. a portable smart device; said portable smart device includes a mobile device app that is configured to enable a user to control and monitor operation of said inflation unit; said portable smart device is configured to wirelessly communicate with said controller in said portable inflation unit; said mobile device app includes at least one exercise program; said portable smart device is a mobile phone, laptop computer, or a tablet;

d. placing said portable BFRT cuff on the user's limb;

e. selecting said exercise program on said mobile device app; said selection of said exercise program is configured to cause said portable smart device to wirelessly send instructions to said portable inflation unit to cause said portable inflation unit to inflate said portable BFRT cuff to a first pressure and then decreasing said pressure in said cuff to a percentage of said first pressure tQ allow a user to thereafter exercise the user's limb while said portable BFRT cuff is inflated about the user's limb; said first pressure is a preprogrammed upper pressure, a detected LOP pressure, or a programmed % LOP; said exercise program is configured to allow a user to select both A) a limb that said portable BFRT cuff is to be releasably connected and B) a % LOP;

f. via said exercise program on said mobile device app, selecting what limb said portable BFRT cuff is placed thereon;

g. causing said portable inflation unit to supply air to said portable BFRT cuff to thereby cause said portable BFRT cuff to inflate until said first pressure is obtained;

h. terminating air flow from portable inflation unit to said portable BFRT cuff after said first pressure has been obtained in said portable BFRT cuff;

i. reducing pressure in said portable BFRT cuff within 0.001-30 seconds after said first pressure has been obtained; said step of reducing pressure continues until said pressure value in said portable BFRT cuff is said preprogrammed upper pressure, said programmed % LOP, or said percent of said preprogrammed upper pressure; said step of reducing pressure is by operation of portable inflation unit;

j. exercising the user's limb while said portable BFRT cuff is positioned on said limb of said user and said pressure in said portable BFRT cuff is said preprogrammed upper pressure, said programmed % LOP, or said percent of said preprogrammed upper pressure;

k. causing said portable inflation unit to remove air from said portable BFRT cuff to reduce pressure in said portable BFRT cuff below said preprogrammed upper pressure, said programmed % LOP, or said percent of said preprogrammed upper pressure after completion of said step of exercising; and l. removing said portable BFRT cuff from the user's limb; and wherein said mobile device app both a) causes said portable inflation unit to reduce said pressure in said portable BFRT cuff when said pressure in said portable BFRT cuff exceeds a preset maximum pressure and b) causes said portable inflation unit to terminate operation after said portable inflation unit operates longer than a preset time period; and wherein said mobile device app allows the user to monitor pressure in said portable BFRT cuff; and wherein said mobile device app is configured to further perform each function selected from the group consisting of i) maintain a log regarding use of said portable BFRT cuff by a user, ii) provide an exercise plan for the user that is using said portable BFRT cuff, iii) record or monitor the progress or compliance of the user's exercise plan with said portable BFRT cuff, iv) select or recommend a BFRT training session for the user, v) keep track of the user's BFRT training sessions, vi) provide suggested training tips for said portable BFRT cuff to the user, vii) provide BFRT information to the user, and viii) transmit or receive data to/from the user's BFRT trainer or instructor.

2. The method as defined in claim 1, further including the step of further deflating said BFRT cuff by said inflation unit after the user completes the exercise of the user's limb, and then removing said portable BFRT cuff from the user's limb.

3. The method as defined in claim 2, further including the step of conducting an ambient air pressure calibration with said pressure sensor in said housing prior to inflating said portable BFRT cuff.

4. The method as defined in claim 3, further including the step of causing pressure in said portable BFRT cuff to be reduced due to inactivity of use of said portable BFRT cuff by said user after a preselect period of time.

5. The method as defined in claim 4, wherein said portable BFRT cuff includes an air release valve; said air chamber is a bladder that includes a polyurethane coating.

6. The method as defined in claim 5, wherein said portable inflation unit includes one or more presets that limits a selection of a) a value of said selected percent of LOP to be between a maximum and minimum preprogrammed percent LOP or b) a value of said selected percent of maximum pressure to be between a maximum and minimum preprogrammed percent of said maximum pressure.

7. The method as defined in claim 1, further including the step of conducting an ambient air pressure calibration with said pressure sensor in said housing prior to inflating said portable BFRT cuff.

8. The method as defined in claim 1, further including the step of causing pressure in said portable BFRT cuff to be reduced due to inactivity of use of said portable BFRT cuff by said user after a preselect period of time.

9. The method as defined in claim 1, wherein said portable BFRT cuff includes an air release valve; said air chamber is a bladder that includes a polyurethane coating.

10. The method as defined in claim 1, wherein said portable inflation unit includes one or more presets that limits a selection of a) a value of said selected percent of LOP to be between a maximum and minimum preprogrammed percent LOP or b) a value of said selected percent of maximum pressure to be between a maximum and minimum preprogrammed percent of said maximum pressure.

* * * * *